(12) United States Patent
Stern et al.

(10) Patent No.: US 10,364,469 B2
(45) Date of Patent: Jul. 30, 2019

(54) GENE EXPRESSION PANEL FOR PROGNOSIS OF PROSTATE CANCER RECURRENCE

(71) Applicants: Illumina, Inc., San Diego, CA (US); University of Southern California, Los Angeles, CA (US)

(72) Inventors: Mariana Carla Stern, Los Angeles, CA (US); Jacek Pinski, Los Angeles, CA (US); Jian-Bing Fan, San Diego, CA (US)

(73) Assignee: ILLUMINA, INC, San Diego, CA (US)

(*) Notice: Subject to any disclaimer, the term of this patent is extended or adjusted under 35 U.S.C. 154(b) by 0 days.

(21) Appl. No.: 15/111,946

(22) PCT Filed: Jan. 16, 2015

(86) PCT No.: PCT/US2015/011824
§ 371 (c)(1),
(2) Date: Jul. 15, 2016

(87) PCT Pub. No.: WO2015/109234
PCT Pub. Date: Jul. 23, 2015

(65) Prior Publication Data
US 2016/0333420 A1 Nov. 17, 2016

Related U.S. Application Data

(60) Provisional application No. 61/928,361, filed on Jan. 16, 2014.

(51) Int. Cl.
*C12Q 1/6886* (2018.01)

(52) U.S. Cl.
CPC ...... *C12Q 1/6886* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| 7,914,988 | B1 | 3/2011 | Chudin et al. | |
|---|---|---|---|---|
| 8,110,363 | B2 | 2/2012 | Chudin et al. | |
| 8,440,407 | B2 | 5/2013 | Chudin et al. | |
| 2003/0036064 | A1 | 2/2003 | Stuelpnagel et al. | |
| 2003/0064366 | A1* | 4/2003 | Hardin | C12Q 1/6869 435/6.11 |
| 2003/0211489 | A1 | 11/2003 | Shen et al. | |
| 2003/0215821 | A1 | 11/2003 | Gunderson et al. | |
| 2004/0018491 | A1 | 1/2004 | Gunderson et al. | |
| 2010/0086935 | A1* | 4/2010 | Bevilacqua | G01N 33/57415 435/6.14 |
| 2011/0071042 | A1* | 3/2011 | Kim | G01N 33/5011 506/9 |
| 2011/0236903 | A1* | 9/2011 | McClelland | C12Q 1/6886 435/6.14 |
| 2012/0028264 | A1* | 2/2012 | Shak | C12Q 1/6886 435/6.14 |
| 2012/0329713 | A1 | 12/2012 | Klem et al. | |

FOREIGN PATENT DOCUMENTS

| WO | WO 2006/066965 A2 | 6/2006 | |
|---|---|---|---|
| WO | WO 2012/015765 A2 | 2/2012 | |
| WO | WO 2012170715 A1 * | 12/2012 | ....... G01N 33/57407 |
| WO | WO 2013/116144 A1 | 8/2013 | |
| WO | WO 2013/184851 A1 | 12/2013 | |
| WO | WO 2014/022594 A1 | 2/2014 | |

OTHER PUBLICATIONS

Simon. Journal of Clinical Oncology. 2005. 23(29):7332-7341.*
Whitehead et al. Genome Biology. 2005. 6(2): Article R13.*
Lapointe et al. PNAS. 2004. 101(3):811-816.*
Hoshikawa et al. Physical Genomics. 2003. 12: 209-219.*
Dhanasekaran et al. Nature. 2001. 412:822-826.*
Singh et al. Cancer Cell. 2002. 1:203-209.*
Glinsky et al. Journal of Clinical Investigation. 2004. 113(6):913-923.*
LaTulippe et al. Cancer Research. 2002. 62:4499-4506.*
PCT Patent Application No. PCT/US2015/011824, filed Jan. 16, 2015; International Search Report / Written Opinion dated Apr. 28, 2015; 11 pages.
Choudhury et al., "The Role of Genetic Markers in the Management of Prostate Cancer", Oct. 1, 2012, *European Urology*, 62(4):577-587.
Erho et al., "Discovery and Validation of a Prostate Cancer Genomic Classifier that Predicts Early Metastasis Following Radical Prostatectomy", Jun. 2013, *PLOS ONE*, 8(6):e66855, 12 pages.
Group TTABPW, "Expression profiling—best practices for data generation and interpretation in clinical trials", Mar. 2004, *Nat Rev Genet*, 5(3):229-37.
Meinshausen et al., "Stability selection", 2010, *J.R. Statist. Soc., Series B*, 72(4):417-473. (Read before the Royal Statistical Society on Feb. 3, 2010.).

(Continued)

*Primary Examiner* — Joseph G. Dauner
(74) *Attorney, Agent, or Firm* — Mueting, Raasch & Gebhardt, P.A.

(57) ABSTRACT

Disclosed is a gene expression panel that can be used to predict prostate cancer (PCa) progression. Some embodiments provide methods for predicting clinical recurrence of PCa. Some embodiments provide a method for predicting progression of prostate cancer in an individual, the method comprising: (a) receiving expression levels of a collection of signature genes from a biological sample taken from said individual, wherein said collection of signature genes comprises at least two genes selected from the group consisting of: NKX2-1, UPK1A, ADRA2C, ABCC11, MMP11, CPVL, ZYG11A, CLEC4F, OAS2, PGC, UPK3B, PCBP3, ABLIM1, EDARADD, GPR81, MYBPC1, F10, KCNA3, GLDC, KCNQ2, RAPGEF1, TUBB2B, MB, DUOXA1, C2orf43, DUOX1, PCA3 and NPR3; (b) applying the expression levels to a predictive model relating expression levels of said collection of signature genes with prostate cancer progression; and (c) evaluating an output of said predictive model to predict progression of prostate cancer in said individual. Systems are also provided for predicting progression and/or recurrence of PCa.

31 Claims, 2 Drawing Sheets

(56) References Cited

OTHER PUBLICATIONS

Nonsrijun et al., "Overexpression of Matrix Metalloproteinase 11 in Thai Prostatic Adenocarcinoma is Associated with Poor Survival", May 30, 2013, *Asian Pacific Journal of Cancer Prevention*, 14(5):3331-3335.

Pepe et al., "Phases of Biomarker Development for Early Detection of Cancer", Jul. 18, 2001, *J Natl Cancer Inst*, 93(14):1054-61.

Ramaswamy et al., "Translating Cancer Genomics into Clinical Oncology", Apr. 29, 2004, *N Engl J Med*, 350:1814-6.

PCT Patent Application No. PCT/US2015/011824, filed Jan. 16, 2015; International Preliminary Report on Patentability dated Jul. 19, 2016; 8 pages.

European Patent Application No. 15701928.2, filed Aug. 10, 2016; First Examination Report dated Sep. 15, 2017, 7 pages.

Nakagawa et al., "A Tissue Biomarker Panel Predicting Systemic Progression after PSA Recurrence Post-Definitive Prostate Cancer Therapy," *PLOS One*, May 2008; 3(5), article e2318.

Ross et al., "Gene Expression Pathways of High Grade Localized Prostate Cancer," *The Prostate*, 2011; 71:1568-78.

Savli et al., "Gene network and canonical pathway analysis in prostate cancer: a microarray study," *Experimental and Molecular Medicine*, Apr. 2008; 40(2):176-185.

Yu et al., "Gene Expression Alternations in Prostate Cancer Predicting Tumor Aggression and Preceding Development of Malignancy," *Journal of Clinical Oncology*, Jul. 2004; 22(14):2790-9.

\* cited by examiner

GENE EXPRESSION PANEL FOR PROGNOSIS OF PROSTATE CANCER RECURRENCE

CROSS-REFERENCE TO RELATED APPLICATIONS

This application is a U.S. National Stage Application of International Application No. PCT/US2015/011824, filed Jan. 16, 2015, which was published in English on Jul. 23, 2015 and International Patent Publication WO 2015/109234 A1. International Application No. PCT/US2015/011824 claims the benefit of and priority to U.S. Provisional Application Ser. No. 61/928,361 filed Jan. 16, 2014. The contents of International Application No. PCT/US2015/011824 and U.S. Provisional Application Ser. No. 61/928,361 are incorporated herein by reference in their entirety and for all purposes.

BACKGROUND

Prostate cancer (PCa) is the most common cancer in American men and is the second leading cause of cancer death. Progress in treating human prostate cancer has been hampered by the finding that histologically identical cancers can exhibit widely variant clinical behavior. For example, in some men diagnosed with prostate cancer, the disease progresses slowly with a prolonged natural history while in other patients, disease progression can be rapid and definitive local therapy can be ineffective.

Improved early detection has resulted in more men being diagnosed with localized prostate cancer (PCa); however, the clinical course of disease after diagnosis is heterogeneous, with recurrence observed in up to one third of patients, even after radical prostatectomy (RP). Therefore, approximately 60% of men diagnosed with low-risk choose to undergo RP as their primary treatment. However, RP may carry potential side effects affecting quality of life, such as incontinence and impotence if nerve-sparing surgery is not possible. Brachytherapy and external-beam radiotherapy are also options for treatment, a choice of primary treatment for approximately 15% of low-risk patients. "Active surveillance" or "watchful waiting" are options that are least favored by most patients, with approximately only ~10% of patients choosing active surveillance in the US. Delayed treatment would be desirable for men with low-risk disease who may have a tumor that will not progress further in order to reduce the negative impact of side effects on health related quality of life. It is reported that approximately 30% of patients who elect for radical prostatectomy have truly low risk of disease recurrence and may benefit more if they opt for "active surveillance" (AS). In contrast, men classified as high risk for PCa-related mortality would benefit from being aggressively treated for their disease at the time of diagnosis, instead of waiting for evidence of disease recurrence to occur. All other patients should undergo and remain on AS unless signs of cancer progression force for definitive local therapy. The PIVOT trial, the first randomized trial comparing men in watchful waiting to men who underwent radical prostatectomy with at least 12 years of follow-up, showed that while only a subgroup of men can benefit from RP, there were no differences seen in risk of metastasis and PCa-related mortality between the groups after 7-9 years of follow-up. Although clinical variables such as Gleason score at biopsy, patient age, PSA level, PSA kinetics (how quickly PSA rises over time), tumor grade and volume have been studied as possible predictors, at this point, no conclusive predictors of PCa progression have been determined.

Even after a radical prostatectomy, up to one third of patients can experience a biochemical recurrence (BCR) (also called PSA recurrence) when serum PSA levels become detectable again. Reports show that 18% to 29% of individuals with BCR can progress to metastatic disease, indicating that BCR is suggestive and not definitive of possible aggressive disease. Therefore, identifying patients at risk of recurrence after RP is also desirable in order to treat them more aggressively after surgery.

Overall, current tools available to determine prognosis for localized PCa patients have limited predictive accuracy. These tools include models and nomograms, intended for easy application in the clinic, that use a combination of clinical variables such as biopsy Gleason score, clinical stage, pre-operative PSA level, and in some models data collected at time of surgery.

SUMMARY

Some embodiments provide a gene expression panel that can be used to predict PCa progression. Some embodiments provide methods for predicting clinical recurrence of PCa. Some embodiments involve obtaining global gene expression profiles from a set of PCa localized intra-capsular tumors. In some embodiments, the tumors are identified from a large cohort of clinically and physiologically well characterized patients diagnosed with PCa.

Some embodiments provide a method for predicting progression of prostate cancer in an individual, the method involves: (a) receiving expression levels of a collection of signature genes from a biological sample taken from said individual, wherein said collection of signature genes includes at least two genes selected from the group including: NKX2-1, UPK1A, ADRA2C, ABCC11, MMP11, CPVL, ZYG11A, CLEC4F, OAS2, PGC, UPK3B, PCBP3, ABLIM1, EDARADD, GPR81, MYBPC1, F10, KCNA3, GLDC, KCNQ2, RAPGEF1, TUBB2B, MB, DUOXA1, C2orf43, DUOX1, PCA3 and NPR3; (b) applying the expression levels to a predictive model relating expression levels of said collection of signature genes with prostate cancer progression; and (c) evaluating an output of said predictive model to predict progression of prostate cancer in said individual. In some embodiments, said collection of signature genes includes at least one gene selected from the group including: NKX2-1, UPK1A, ABCC11, MMP11, CPVL, ZYG11A, CLEC4F, OAS2, PGC, UPK3B, PCBP3, EDARADD, GPR81, MYBPC1, KCNA3, GLDC, KCNQ2, RAPGEF1, TUBB2B, MB, DUOXA1, C2orf43, DUOX1, and NPR3. In some embodiments, said collection of signature genes includes at least two genes selected from the group including: NKX2-1, UPK1A, ADRA2C, ABCC11, MMP11, CPVL, ZYG11A, CLEC4F, OAS2, and PGC. In some embodiments, said collection of signature genes includes at least two genes selected from the group including: ZYG11A, MMP11, MYBPC1, DUOX1, EDARADD, PGC, GPR81, NKX2-1, ABLIM1, and ABCC11.

In some embodiments, the output of the predictive model predicts a likelihood of clinical recurrence of prostate cancer in the individual after the individual has undergone treatment for prostate cancer. In some embodiments, the output of the predictive model predicts a likelihood of biochemical recurrence of prostate cancer in the individual after the individual has undergone treatment for prostate cancer.

In some embodiments, the methods described above further involve providing a report having a prediction of clinical recurrence of prostate cancer of the individual.

In some embodiments, the methods described above further involve applying at least one of Gleason score, year of surgical operation for prostate cancer, pre-operative PSA level, and age to the predictive model, wherein the predictive model relates the at least one of Gleason score, year of surgical operation for prostate cancer, pre-operative PSA level, and age to prostate cancer progression.

In some embodiments, the methods described above further involve combining the gene expression levels of the signature genes with one or more other biomarkers to predict progression of prostate cancer in the individual. In some embodiments, the one or more other biomarkers are selected from the group consisting of germline mutations, somatic mutations, DNA methylation markers, protein markers, and any combinations thereof.

In some implementations of the methods described above, the expression levels of a collection of signature genes include gene expression levels measured at multiple times. In some implementations, the methods further involve using the dynamics of the gene expression levels measured at multiple times to predict progression of prostate cancer in the individual.

In some embodiments, the methods described above further involve evaluating the output of the predictive model to determine whether or not the individual falls in a high risk group. In some embodiments, the methods described above further involve developing the predictive model by selecting the collection of signature genes from more than about 1000 genes. In some embodiments, the methods described above further involve developing the predictive model using stability selection. In some embodiments, the methods described above further involve developing the predictive model using logistic regression.

In some implementations, the methods described above further involve developing the predictive model by selecting genes using stability selection with elastic-net regularized logistic regression.

In some implementations, applying the expression levels of the collection of signature genes to the predictive model involves weighting the expression levels according to stability rankings or predictive power rankings of the collection of signature genes.

In some implementations, the predictive model has an area under the curve that is larger than that of a predictive model having only Gleason score.

In some implementations, the predictive model has an area under the curve that is larger than that of a predictive model having only Gleason score, pre-operative PSA level, and age.

In some implementations, the methods described above further involve determining the expression levels prior to (a). In some implementations, determining the expression levels involves: obtaining proteins or expressed nucleic acids from the biological sample; and determining amounts of the expressed nucleic acids for sequences of the signature genes. The amounts of the expressed nucleic acids may be determined by performing quantitative PCR on nucleic acids having sequences of the expressed nucleic acids from the biological sample; applying nucleic acids having sequences of the expressed nucleic acids from the biological sample to nucleic acid array; and/or sequencing nucleic acids using a next generation sequencing technique. Some implementations further involve random priming of mRNA to produce cDNA, hybridizing the produced cDNA to oligonucleotides corresponding to the signature genes, extending the oligonucleotides, and/or ligating the oligonucleotides. In some implementations, the method further involves fluorescently labeling the oligonucleotides in qPCR and determining the expression levels of the signature genes based on fluorescence levels of the labeled oligonucleotides.

In some implementations, the biological sample includes a prostate tissue sample from the individual. In some implementations, the biological sample includes circulating tumor cells (CTCs) isolated from at least one body fluid of the individual. In some implementations, the at least one body fluid is selected from the group consisting of blood, saliva, urine, and any combinations thereof. In some implementations, the biological sample includes exosomes of the individual. In some implementations, the biological sample comprises circulating tumor nucleic acids of the individual.

In some implementations, the methods above further involve microdissecting a prostate tissue sample using a laser capture microdissection (LCM).

Some implementations provide system for predicting progression of prostate cancer in an individual, the system includes: an apparatus configured to determine expression levels of nucleic acids from a biological sample taken from the individual; and hardware logic designed or configured to perform operations of any of the method described above.

INCORPORATION BY REFERENCE

All patents, patent applications, and other publications, including all sequences disclosed within these references, referred to herein are expressly incorporated herein by reference, to the same extent as if each individual publication, patent or patent application was specifically and individually indicated to be incorporated by reference. All documents cited are, in relevant part, incorporated herein by reference in their entireties for the purposes indicated by the context of their citation herein. However, the citation of any document is not to be construed as an admission that it is prior art with respect to the present disclosure.

DETAILED DESCRIPTION

Definitions

Figure 1:
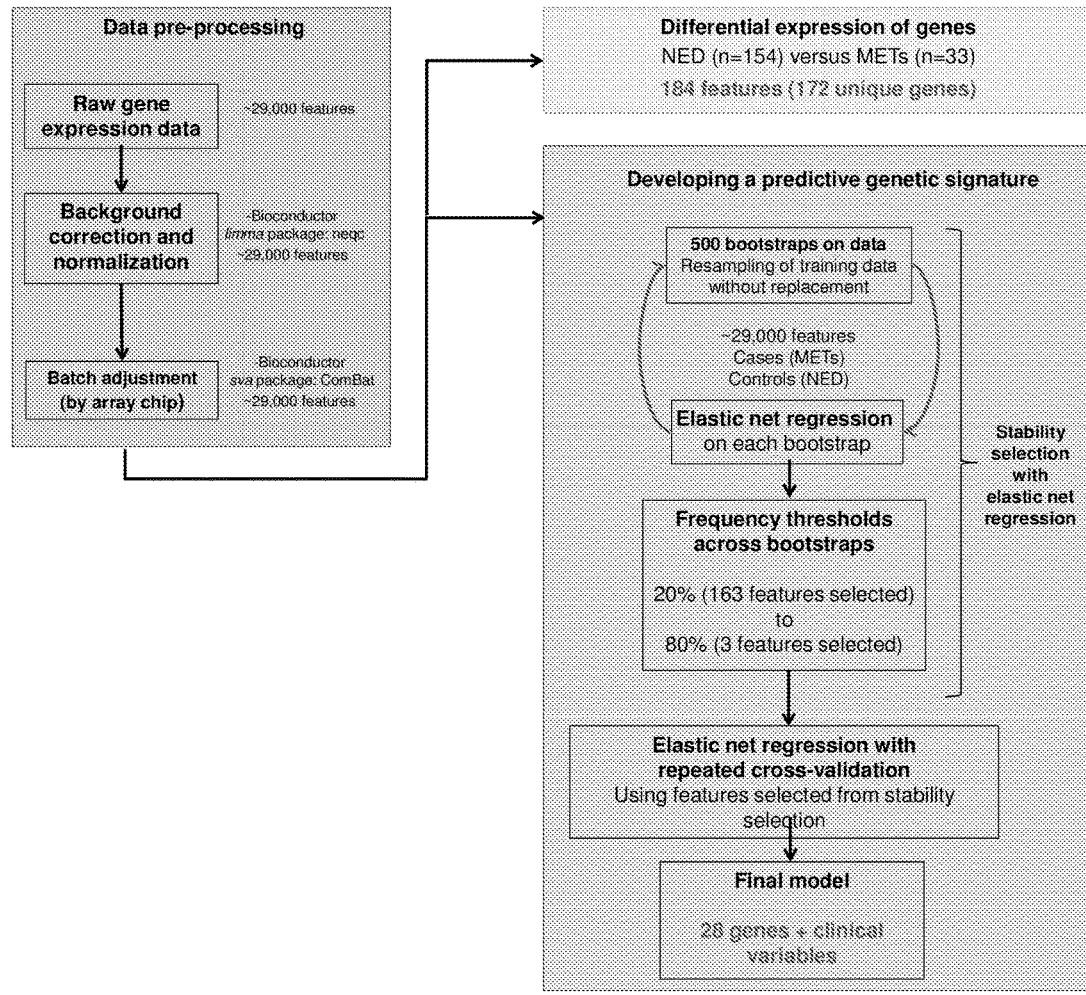
FIG. 1 is a flowchart showing a summary of the methods used for differential expression analysis and predictive model development how different operations in processing test samples may be grouped to be handled by different elements of a system.

Unless otherwise indicated, the practice of the method and system disclosed herein involves conventional techniques and apparatus commonly used in molecular biology, microbiology, protein purification, protein engineering, protein and DNA sequencing, and recombinant DNA fields, which are within the skill of the art. Such techniques and apparatus are known to those of skill in the art and are described in numerous texts and reference works (See e.g., Sambrook et al., "Molecular Cloning: A Laboratory Manual," Third Edition (Cold Spring Harbor), [2001]); and Ausubel et al., "Current Protocols in Molecular Biology" [1987]).

Numeric ranges are inclusive of the numbers defining the range. It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Unless defined otherwise herein, all technical and scientific terms used herein have the same meaning as commonly understood by one of ordinary skill in the art. Various scientific dictionaries that include the terms included herein are well known and available to those in the art. Although any methods and materials similar or equivalent to those described herein find use in the practice or testing of the embodiments disclosed herein, some methods and materials are described.

The terms defined immediately below are more fully described by reference to the Specification as a whole. It is to be understood that this disclosure is not limited to the particular methodology, protocols, and reagents described, as these may vary, depending upon the context they are used by those of skill in the art.

The headings provided herein are not intended to limit the disclosure.

As used herein, the singular terms "a," "an," and "the" include the plural reference unless the context clearly indicates otherwise.

"Nucleic acid sequence," "expressed nucleic acid," or grammatical equivalents thereof used in the context of a corresponding signature gene means a nucleic acid sequence whose amount is measured as an indication of the gene's expression level. The nucleic acid sequence can be a portion of a gene, a regulatory sequence, genomic DNA, cDNA, RNA including mRNA and rRNA, or others. A preferred embodiment utilizes mRNA as the primary target sequence. As is outlined herein, the nucleic acid sequence can be a sequence from a sample, or a secondary target such as, for example, a product of a reaction such as a detection sequence from an invasive cleavage reaction, a ligated probe from an OLA or DASL (cDNA-mediated Annealing, Selection, and Ligation) reaction, an extended probe from a PCR reaction, or PCR amplification product (e.g., "amplicon"). A nucleic acid sequence corresponding to a signature gene can be any length, with the understanding that longer sequences are more specific. Probes are made to hybridize to nucleic acid sequences to determine the presence or absence of expression of a signature gene in a sample.

"Prostate cancer" as used herein includes carcinomas, including, carcinoma in situ, invasive carcinoma, metastatic carcinoma and pre-malignant conditions.

As used herein the term "comprising" means that the named elements are included, but other element (e.g., unnamed signature genes) may be added and still represent a composition or method within the scope of the claim. The transitional phrase "consisting essentially of" means that the associated composition or method encompasses additional elements, including, for example, additional signature genes, that do not affect the basic and novel characteristics of the disclosure.

As used herein, the term "signature gene" refers to a gene whose expression is correlated, either positively or negatively, with disease extent or outcome or with another predictor of disease extent or outcome. In some embodiments, a gene expression score (GEX) can be statistically derived from the expression levels of a set of signature genes and used to diagnose a condition or to predict clinical course. In some embodiments, the expression levels of the signature gene may be used to predict progression of PCa without relying on a GEX. A "signature nucleic acid" is a nucleic acid comprising or corresponding to, in case of cDNA, the complete or partial sequence of a RNA transcript encoded by a signature gene, or the complement of such complete or partial sequence. A signature protein is encoded by or corresponding to a signature gene of the disclosure.

The term "relapse prediction" is used herein to refer to the prediction of the likelihood of cancer recurrence in patients with no apparent residual tumor tissue after treatment. The predictive methods of the present disclosure can be used clinically to make treatment decisions by choosing the most appropriate treatment modalities for any particular patient. The predictive methods of the present disclosure also can provide valuable tools in predicting if a patient is likely to respond favorably to a treatment regimen, such as surgical intervention, chemotherapy with a given drug or drug combination, and/or radiation therapy.

The Gleason grading system is based on the glandular pattern of the tumor. Gleason grade takes into account the ability of the tumor to form glands. A pathologist, using relatively low magnification, performs the histologic review necessary for assigning the Gleason grade. The range of grades is 1-5: 1, 2 and 3 are considered to be low to moderate in grade; 4 and 5 are considered to be high grade. The prognosis for a given patient generally falls somewhere between that predicted by the primary grade and a secondary grade given to the second most prominent glandular pattern. When the two grades are added the resulting number is referred to as the "Gleason score". The Gleason Score is a more accurate predictor of outcome than either of the individual grades. Thus, the traditionally reported Gleason score will be the sum of two numbers between 1-5 with a total score from 2-10. It is unusual for the primary and secondary Gleason grade to differ by more than one, such that the only way that there can be a Gleason score 7 tumor is if the primary or secondary Gleason grade is 4. Because of the presence of grade 4 glandular patterns in tissue having Gleason score 7, these tumors can behave in a much more aggressive fashion than those having Gleason score 6. In a recent study of over 300 patients, the disease specific survival for Gleason score 7 patients was 10 years. In contrast, Gleason score 6 patients survived 16 years and Gleason 4-5 for 20 years. It is therefore clear that the prognosis for men with Gleason score 7 tumors is worse than for men with Gleason score 5 and 6 tumors. Under certain circumstances it is suggested that men with Gleason 7 tumors can be considered for clinical trials.

The term "plurality" refers to more than one element. For example, the term is used herein in reference to a number of nucleic acid molecules or sequence tags that is sufficient to identify significant differences in copy number variations in test samples and qualified samples using the methods disclosed herein. In some embodiments, at least about $3 \times 10^6$ sequence tags of between about 20 and 40 bp are obtained for each test sample. In some embodiments, each test sample provides data for at least about $5 \times 10^6$, $8 \times 10^6$, $10 \times 10^6$, $15 \times 10^6$, $20 \times 10^6$, $30 \times 10^6$, $40 \times 10^6$, or $50 \times 10^6$ sequence tags, each sequence tag comprising between about 20 and 40 bp.

The terms "polynucleotide," "nucleic acid" and "nucleic acid molecules" are used interchangeably and refer to a covalently linked sequence of nucleotides (i.e., ribonucleotides for RNA and deoxyribonucleotides for DNA) in which the 3' position of the pentose of one nucleotide is joined by a phosphodiester group to the 5' position of the pentose of the next. The nucleotides include sequences of any form of nucleic acid, including, but not limited to RNA and DNA molecules. The term "polynucleotide" includes, without limitation, single- and double-stranded polynucleotide.

The term "Next Generation Sequencing (NGS)" herein refers to sequencing methods that allow for massively parallel sequencing of clonally amplified molecules and of single nucleic acid molecules. Non-limiting examples of NGS include sequencing-by-synthesis using reversible dye terminators, and sequencing-by-ligation.

The term "read" refers to a sequence read from a portion of a nucleic acid sample. Typically, though not necessarily, a read represents a short sequence of contiguous base pairs in the sample. The read may be represented symbolically by the base pair sequence (in ATCG) of the sample portion. It may be stored in a memory device and processed as appropriate to determine whether it matches a reference sequence or meets other criteria. A read may be obtained directly from a sequencing apparatus or indirectly from stored sequence information concerning the sample. In some cases, a read is a DNA sequence of sufficient length (e.g., at least about 25 bp) that can be used to identify a larger sequence or region, e.g., that can be aligned and specifically assigned to a chromosome or genomic region or gene.

As used herein, the terms "aligned," "alignment," or "aligning" refer to the process of comparing a read or tag to a reference sequence and thereby determining whether the reference sequence contains the read sequence. If the reference sequence contains the read, the read may be mapped to the reference sequence or, in certain embodiments, to a particular location in the reference sequence. In some cases, alignment simply tells whether or not a read is a member of a particular reference sequence (i.e., whether the read is present or absent in the reference sequence). For example, the alignment of a read to the reference sequence for human chromosome 13 will tell whether the read is present in the reference sequence for chromosome 13. A tool that provides this information may be called a set membership tester. In some cases, an alignment additionally indicates a location in the reference sequence where the read or tag maps to. For example, if the reference sequence is the whole human genome sequence, an alignment may indicate that a read is present on chromosome 13, and may further indicate that the read is on a particular strand and/or site of chromosome 13.

Aligned reads or tags are one or more sequences that are identified as a match in terms of the order of their nucleic acid molecules to a known sequence from a reference genome. Alignment can be done manually, although it is typically implemented by a computer algorithm, as it would be impossible to align reads in a reasonable time period for implementing the methods disclosed herein. One example of an algorithm from aligning sequences is the Efficient Local Alignment of Nucleotide Data (ELAND) computer program distributed as part of the Illumina Genomics Analysis pipeline. Alternatively, a Bloom filter or similar set membership tester may be employed to align reads to reference genomes. See U.S. Patent Application No. 61/552,374 filed Oct. 27, 2011 which is incorporated herein by reference in its entirety. The matching of a sequence read in aligning can be a 100% sequence match or less than 100% (non-perfect match).

The term "mapping" used herein refers to specifically assigning a sequence read to a larger sequence, e.g., a reference genome, by alignment.

As used herein, the term "reference genome" or "reference sequence" refers to any particular known genome sequence, whether partial or complete, of any organism or virus which may be used to reference identified sequences from a subject. For example, a reference genome used for human subjects as well as many other organisms is found at the National Center for Biotechnology Information at ncbi.nlm.nih.gov. A "genome" refers to the complete genetic information of an organism or virus, expressed in nucleic acid sequences.

In various embodiments, the reference sequence is significantly larger than the reads that are aligned to it. For example, it may be at least about 100 times larger, or at least about 1000 times larger, or at least about 10,000 times larger, or at least about $10^5$ times larger, or at least about $10^6$ times larger, or at least about $10^7$ times larger.

The term "based on" when used in the context of obtaining a specific quantitative value, herein refers to using another quantity as input to calculate the specific quantitative value as an output.

As used herein the term "chromosome" refers to the heredity-bearing gene carrier of a living cell, which is derived from chromatin strands comprising DNA and protein components (especially histones). The conventional internationally recognized individual human genome chromosome numbering system is employed herein.

The term "subject" herein refers to a human subject as well as a non-human subject such as a mammal, an invertebrate, a vertebrate, a fungus, a yeast, a bacterium, and a virus. Although the examples herein concern humans and the language is primarily directed to human concerns, the concepts disclosed herein are applicable to genomes from any plant or animal, and are useful in the fields of veterinary medicine, animal sciences, research laboratories and such.

The term "condition" herein refers to "medical condition" as a broad term that includes all diseases and disorders, but can include [injuries] and normal health situations, such as pregnancy, that might affect a person's health, benefit from medical assistance, or have implications for medical treatments.

The term "sensitivity" as used herein is equal to the number of true positives divided by the sum of true positives and false negatives.

The term "specificity" as used herein is equal to the number of true negatives divided by the sum of true negatives and false positives.

The term "enrich" herein refers to the process of amplifying nucleic acids contained in a portion of a sample. Enrichment includes specific enrichment that targets specific sequences, e.g., polymorphic sequences, and non-specific enrichment that amplifies the whole genome of the DNA fragments of the sample.

The term "primer," as used herein refers to an isolated oligonucleotide that is capable of acting as a point of initiation of synthesis when placed under conditions inductive to synthesis of an extension product (e.g., the conditions include nucleotides, an inducing agent such as DNA polymerase, and a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer, use of the method, and the parameters used for primer design.

INTRODUCTION

A need exists for large-scale discovery, validation, and clinical application of mRNA biosignatures of disease and for methods of genomic analysis in patients with established clinical prostate cancer disease to predict disease outcomes. The present disclosure satisfies this need and provides related advantages. Some embodiments provide a gene expression panel that can be used to predict PCa progression. Some embodiments provide methods for predicting clinical recurrence of PCa. Some embodiments involve obtaining global gene expression profiles from a set of PCa localized intra-capsular tumors.

Given the negative impact of many of the available treatments on patient health related quality of life, and the trend for more men to be diagnosed at a younger age, active surveillance and delayed treatment would be desirable for a larger proportion of men with low risk disease. Conversely, adjuvant treatments with androgen ablation and/or chemotherapy could improve clinical outcome in those patients with localized disease at higher risk of developing recurrence. Having improved risk prediction models would offer stronger re-assurance to low-risk patients, which will reduce over-treatment of indolent disease, lower the financial burden on patients, and improve the quality of life among these PCa cancer survivors. This disclosure provides improved predictive models that incorporate tumor biomarkers and that better distinguish between indolent cases and metastatic disease. The development of such models was challenged by the lack of sufficient databases that include appropriate tissue for biomarker identification and long-term clinical data. Moreover, until recently the available technologies precluded the use of archival formalin-fixed paraffin embedded (FFPE) tumor tissue for biomarkers identification.

Some embodiments of this disclosure address the deficiencies of previous methods, and maximize the opportunities to identify gene expression profiles predictive of clinical outcomes, while minimizing the impact of PCa tumor heterogeneity. In some embodiments, a predictive model for determining PCa progression is developed. In developing the predictive model, some embodiments involve isolating RNA from laser-captured microdissected malignant epithelial glands using consecutive slides from PCa tumors in order to enrich samples for the target cells of interest, minimizing contamination by non-tumoral cells. In some embodiments, the model development makes use of samples for glands representative of the overall Gleason score of each patients. In some embodiments, expression analyses are performed using the DASL (cDNA-mediated annealing, selection, extension and ligation assay) whole genome profiling platform (Illumina). In some embodiments, expression profiles from tumors from patients with and without PCa clinical recurrence are used to develop the predictive model. In some embodiments, the two patient groups have been appropriately matched taking into account follow-up time.

Some embodiments provide a method for predicting progression of prostate cancer in an individual, the method comprising: (a) receiving expression levels of a collection of signature genes from a biological sample taken from said individual, wherein said collection of signature genes comprises at least two genes selected from the group consisting of: NKX2-1, UPK1A, ADRA2C, ABCC11, MMP11, CPVL, ZYG11A, CLEC4F, OAS2, PGC, UPK3B, PCBP3, ABLIM1, EDARADD, GPR81, MYBPC1, F10, KCNA3, GLDC, KCNQ2, RAPGEF1, TUBB2B, MB, DUOXA1, C2orf43, DUOX1, PCA3 and NPR3; (b) applying the expression levels to a predictive model relating expression levels of said collection of signature genes with prostate cancer progression; and (c) evaluating an output of said predictive model to predict progression of prostate cancer in said individual. In some embodiments, the output of the predictive model predicts a likelihood of clinical recurrence of prostate cancer in the individual after said individual has undergone treatment for prostate cancer.

In some embodiments, the 28 markers of the panel are differentially expressed/regulated between PCa cases with and without recurrence, and are predictive of aggressive disease. In some embodiments, the predictive models include these 28 markers along with pre-operative PSA levels, Gleason score, and age at diagnosis, which models show greater prediction than models having clinical variables alone. One skilled in the art understands that further validation of the models using additional datasets will allow improvement of the predictive power of the models, which may include different coefficients of the models. In some embodiments, one or more genes can be selected from the panel to form predictive models for evaluation of PCa progression.

The sensitivity and specificity of the molecular signature derived from the 28 signature genes mentioned above, or subset thereof, has utility for patients undergoing prostate biopsy for diagnosis of carcinoma based on applicability of the methods described herein to diagnosis as well as prognosis through biopsy samples. Furthermore, the present disclosure enables the development of a diagnostic test that is technically simple and applicable for routine clinical use, and incorporation into existing prostate cancer nomograms (Group TTABPW, *Nat Rev Genet* 5:229-37 (2004); Ramaswamy, *N Engl J Med* 350:1814-6 (2004); Sullivan Pepe et al. *J Natl Cancer Inst* 93:1054-61 (2001)).

Identifying Gene Expression Panel and Developing Predictive Model

Some embodiments the disclosure provides methods for developing predictive models for determining PCa progression. In some embodiments, the models are developed using data collected from patients known to have prostate cancer. In some embodiments, the patients providing the data underwent radical retropubic prostatectomy and lymph node dissection. In some embodiments, the data for developing the predictive models may be obtained from archival formalin-fixed paraffin embedded (FFPE) prostate tumor tissues. In some embodiments, the predictive models describe the correlation between expression levels of signature genes measured in prostate tumor tissues and clinical recurrence of PCa in patients providing the tumor tissues. In various embodiments, the disclosure provides a panel of 28 signature genes that correlate with PCa recurrence in the patients, as shown in Table 2: NKX2-1, UPK1A, ADRA2C, ABCC11, MMP11, CPVL, ZYG11A, CLEC4F, OAS2, PGC, UPK3B, PCBP3, ABLIM1, EDARADD, GPR81, MYBPC1, F10, KCNA3, GLDC, KCNQ2, RAPGEF1, TUBB2B, MB, DUOXA1, C2orf43, DUOX1, PCA3 and NPR3. Among the 28 signature genes shown in Table 2 and Table 3, ABLIM1, ADRA2C, PCA3, F10 have been reported to be associated with PCa progression and/or metastasis. In some embodiments, the disclosure further provides methods to predict PCa development, recurrence, and/or survival for an individual using the individual's expression levels of one or more of the signature genes. In some embodiments, the predictive model includes the expression levels of at least one gene that is selected from the group including: NKX2-1, UPK1A, ABCC11, MMP11, CPVL, ZYG11A, CLEC4F, OAS2, PGC, UPK3B, PCBP3, EDARADD, GPR81, MYBPC1, KCNA3, GLDC, KCNQ2, RAPGEF1, TUBB2B, MB, DUOXA1, C2orf43, DUOX1, and NPR3.

In some embodiments, raw gene expression levels microarray data may be obtained from the whole genome DASL HT platform (Illumina, San Diego, Calif.). In some embodiments, the gene expression data may be preprocessed by normalization, background correction, and/or batch effect correction. The preprocessed data may then be analyzed for differential expression of genes for no evidence of disease (NED) group versus clinical recurrence (CR) group.

In some embodiments, to develop a predictive model for aggressive PCa one may use only clinical recurrence cases versus NED (neither clinical nor PSA) controls. In some embodiments, one may also compare PSA (i.e., BCR) recurrence versus no recurrence to develop a predictive model, e.g., for determining the likelihood of developing PCa or response to PCa treatment. In some embodiments, the probes included in the final model are selected from an entire set of ~29K probes using stability selection with elastic-net regularized logistic regression. Elastic-net regression is a high dimensional regression method that incorporates both a LASSO ($L_1$) and a ridge regression ($L_2$) regularization penalty. The exact mix of penalties (LASSO vs. ridge) is controlled by a parameter $0 \leq \alpha \leq 1$ ($\alpha=0$ is pure ridge regression and $\alpha=1$ is pure LASSO). The degree of regularization is controlled by the single penalty parameter. Both LASSO and ridge regression shrink the model coefficients toward zero relative to unpenalized regression but LASSO can shrink coefficients to exactly zero, thus effectively performing variable selection. LASSO alone however, tends to select randomly among correlated predictors, which the addition of the ridge penalty helps prevent. In some embodiments, one may use the implementation of elastic-net logistic regression in the R package 'glmnet.'

The idea behind stability selection is to find 'stable' probes that consistently show to be predictive of recurrence across multiple data sets obtained by 'perturbing' the original data. Specifically, perturbed versions of the data are obtained by subsampling m<n subjects (n is the total number of subjects) without replacement. Regularized regression (or elastic-net in some embodiments) is then performed on each subsample version of the data to obtain the complete regularized path (i.e. the model coefficients as a function of the regularization penalty). The effect of the LASSO penalty is to shrink the vast majority of the probe coefficients to exactly zero; the probes with non-zero coefficients (predictive) across a sizable proportion of the subsample versions of the data are deemed stable predictors.

In some embodiments, to implement stability selection with elastic net regression, one may calibrate the tuning parameter $\alpha$ using repeated cross-validation (e.g., using R package caret for a 10-fold cross-validation). In some embodiments, the tuning parameter $\alpha=0.3$ may provide good prediction based on the resulting AUC metric. In some embodiments, since the intention is to include as many possible features while maintaining good prediction, $\alpha=0.2$ may be used for the final model selection using stability selection (smaller $\alpha$ yields larger models) which a may yield a similar or marginally smaller AUC. In some embodiments, stability selection may be implemented using 500, 1000, 2000, or other numbers of subsamples of the data, each having half of the total sample size (each with roughly the same proportion of cases and controls as the original), in order to identify robust predictors for the final model. In some embodiments, standardization of the gene expression levels by their standard deviation (the default in glmnet to place all gene features on the same scale) is not done, since differential variability of the gene expression levels may be biologically important. In some embodiments, such standardization may be performed. In some embodiments, clinical variables such as Gleason score and PSA level are force included (i.e. not subject to the elastic net regularization penalty). In some embodiments, clinical variables may be left out of the predictive models. In some embodiments, stable probes can be obtained for stability thresholds (proportion of the 500 or larger numbers of subsamples in which the probe has a non-zero coefficient) ranging from 20% to 80%. Larger or smaller range of stability thresholds may be applied in other embodiments.

In some embodiments, a panel of signature genes is identified for a predictive model for prostate cancer clinical recurrence. As shown in the example below, the panel of signature genes includes 28 genes shown in Table 2. A summary of the methods used for differential expression analysis and predictive model development are shown in FIG. 1.

In some embodiments, one or more of the genes shown in Table 2 may be used in a predictive model. In some embodiments, the one or more genes may be selected by their correlation with recurrence in the training data set to develop the predictive models. In some embodiments, the one or more genes may be selected by their reliability ranks. In some embodiments, the panel of signature genes include at least 1, 2, 3, 4, 5, 6, 7, 8, 9, or 10 of NKX2-1, UPK1A, ADRA2C, ABCC11, MMP11, CPVL, ZYG11A, CLEC4F, OAS2, and PGC. In some embodiments, the one or more genes may be selected by their predictive power rankings. In some embodiments, the panel of signature genes include at least 1, 2, 3, 4, 5, 6, 7, 8, 9, or 10 of ZYG11A, MMP11, MYBPC1, DUOX1, EDARADD, PGC, GPR81, NKX2-1, ABLIM1, and ABCC11.

In some embodiments, based on the expression levels for the set of probes determined by stability selection and the clinical variables, the predictive model is obtained by fitting logistic model using elastic-net regularized logistic regression. If p is the probability of clinical recurrence given the covariates (expression levels and clinical variables), the model has the form:

$$\log\left(\frac{p}{1-p}\right) = \sum_{i=1}^{28} coeff_i \times expr\ level_i + coeff_{age} \times age + coeff_{PSA} \times PSA\ level +$$

$$coeff_{Gleason} \times Gleason\ Score + coeff_{year} \times Operation\ Year$$

where expr level$_i$ represents the expression level for probe i, and coeff$_i$ represents the corresponding coefficient; PSA level represents the PSA level, and coeff$_{PSA}$ its coefficient; Age represents the age of the patient at diagnosis and coeff$_{age}$ its coefficient. Gleason Score and Operation Year are discrete multilevel variables with 3 and 9 levels respectively. Thus, in the equation above Gleason Score is represented by 3-1 indicator (dummy) variables, and $\text{Coeff}_{Gleason}$ represents the corresponding 3-1 coefficients. Similarly, Operation Year is represented by 9-1 dummy variables. Thus, there are actually 3 terms for Gleason score and 9 terms for operation year. Each of those terms has a 0/1 dummy variable and associated coefficient. Table 5 shows all coefficients developed for a preliminary model.

In some embodiments, instead of selecting a subset of genes from the panel, a model may weight the genes differently in the logistic regression. In some embodiments, predicting the progression of PCa for an individual involves applying expression levels of the collection of signature genes to the predictive model, which involves weighting said expression levels according to stability rankings of the collection of signature genes. In some embodiments, the method involves weighting expression levels according to predictive power rankings of the collection of signature genes.

The logistic regression model above expresses the specific way the expression levels and the clinical variables are combined to obtain a score for each individual. In some embodiments, expression levels are weighted in the elastic-net regularized logistic regression. The weighting here does not refer to the model coefficients (which can be thought of as weights for the expression levels and clinical variables), but rather to an additional mechanism for differentially accounting for variable importance in the logistic regression procedure. In this regard, alternative embodiments consider unweighted logistic regression, i.e. treating all genes equally, and weighted logistic regression, weighting by the stability selection frequencies.

In some embodiments, various clinical variables (e.g., PSA level, Gleason score, operation year and age) will be included in the same logistic model along with the signature genes. Coefficients will be defined for each variable (gene expression and clinical values). This logistic regression model will provide a probability of having a clinical recurrence given the provided gene expression scores and clinical variables. This probability will be a number between 0-1, and it will indicate for each given patient the probability of having a clinical recurrence.

In some embodiments, in addition to identifying the coefficients of the predictive model, the disclosure identifies the most useful specificity and sensitivity a user wishes to have for a specific risk probability. Based on the desired specificity and sensitivity levels, the method will report the risk status of each patient. For example, we may find that given the specificity and sensitivity of our model, a patient with 45% chance of clinical recurrence might be better off being classified as high-risk of recurrence rather than low-risk or vice versa. In other words, more user-friendly criteria can be chosen based on more detailed analyses in further datasets to determine the most practical interpretation of the risk probability depending on how much clinicians want to risk having a false positive or a false negative.

One skilled in the art can readily determine other combinations of signature genes sufficient to practice the disclosures claimed herein. For example, based on the stability selection ranking of Table 2 or the p-values of the univariate comparison between the NED and the CR groups, one skilled in the art can readily determine a sub-combination of prostate cancer signature genes suitable for methods of the disclosure. Those exemplary genes having lowest stability selection ranks can be excluded, with the remaining genes providing a sufficient collection of isolated prostate cancer signature genes suitable for relapse prediction of prostate cancer. Similarly, genes having the largest p-value may be excluded. For example, the NPR3 gene ranks the lowest in stability selection percentage, and therefore removing the NPR3 gene is expected to have the least effect on overall predictive power of the model. Similarly, F10 has the largest p-value, indicating smallest difference between the NED and CR groups. Removing F10 from the model is expected to have the least effect on overall accuracy of the model. One skilled in the art can readily recognize these or other appropriate genes that can be omitted from the 28 identified prostate cancer signature genes and still be sufficient for methods of the disclosure.

Alternatively, one skilled in the art can remove any one or a few of the 28 identified prostate cancer signature genes so long as those remaining provide a sufficient statistical correlation for use in methods of the disclosure. Exemplary collections of prostate cancer signature genes include, for example, those set forth elsewhere herein. It is readily recognized by one skilled in the art that these listed combinations are merely exemplary and that any of a number of such combinations can readily be determined by one skilled in the art. It is understood that, given the set of 28 signature genes, removal of a single signature gene, will likely not have a big impact on the overall performance of the model having many other genes.

Thus, the disclosure provides a method of predicting prostate cancer relapse based on the expression patterns for any subset of the 28 genes set forth in Table 2 including, for example, at least 1, 2, 3, 4, 5, 6, 7, 8, 9, 10, 11, 12, 13, 14, 15, 16, 17, 18, 19, 20, 21, 22, 23, 24, 25, 26 or 27 of the 28 genes. The disclosure also provides a method of predicting prostate cancer relapse based on the expression patterns for any subset of the set of genes consisting of NKX2-1, UPK1A, ABCC11, MMP11, CPVL, ZYG11A, CLEC4F, OAS2, PGC, UPK3B, PCBP3, EDARADD, GPR81, MYBPC1, KCNA3, GLDC, KCNQ2, RAPGEF1, TUBB2B, MB, DUOXA1, C2orf43, DUOX1, and NPR3. In some embodiments, the disclosure also provides a method of predicting prostate cancer progression based on the expression patterns for any subset of the set of genes consisting of NKX2-1, UPK1A, ADRA2C, ABCC11, MMP11, CPVL, ZYG11A, CLEC4F, OAS2, and PGC. In some embodiments, the disclosure also provides a method of predicting prostate cancer progression based on the expression patterns for any subset of the set of genes consisting of ZYG11A, MMP11, MYBPC1, DUOX1, EDARADD, PGC, GPR81, NKX2-1, ABLIM1, and ABCC11.

While the present disclosure is disclosed and exemplified with the 28 signature genes set forth above and shown in Table 2, the methods are universally applicable to the diagnosis and prognosis of a broad range of cancers and other conditions. The skilled person apprised of the disclosure disclosed herein will appreciate that any known predictor of disease extent for any condition can be selected to establish a risk score for prognosis of relapse that can be more accurate or sensitive than relapse prediction solely based on the known predictor alone.

Individuals suspected of having any of a variety of diseases or conditions, such as cancer, can be evaluated using a method of the disclosure. Exemplary cancers that can be evaluated using a method of the disclosure include, but are not limited to hematoporetic neoplasms, Adult T-cell leukemia/lymphoma, Lymphoid Neoplasms, Anaplastic large cell lymphoma, Myeloid Neoplasms, Histiocytoses, Hodgkin Diseases (HD), Precursor B lymphoblastic leukemia/lymphoma (ALL), Acute myclogenous leukemia (AML), Precursor T lymphoblastic leukemia/lymphoma (ALL), Myclodysplastic syndromes, Chronic Mycloproliferative disorders, Chronic lymphocytic leukemia/small lymphocytic lymphoma (SLL), Chronic Myclogenous Leukemia (CML), Lymphoplasmacytic lymphoma, Polycythemia Vera, Mantle cell lymphoma, Essential Thrombocytosis, Follicular lymphoma, Myelofibrosis with Myeloid Metaplasia, Marginal zone lymphoma, Hairy cell leukemia, Hemangioma, Plasmacytoma/plasma cell myeloma, Lymphangioma, Glomangioma, Diffuse large B-cell lymphoma, Kaposi Sarcoma, Hemanioendothelioma, Burkitt lymphoma, Angiosarcoma, T-cell chronic lymphocytic leukemia, Hemangiopericytoma, Large granular lymphocytic leukemia, head & neck cancers, Basal Cell Carcinoma, Mycosis fungoids and sezary syndrome, Squamous Cell Carcinoma, Ceruminoma, Peripheral T-cell lymphoma, Osteoma, Nonchromaffin Paraganglioma, Angioimmunoblastic T-cell lymphoma, Acoustic Neurinoma, Adenoid Cystic Carcinoma, Angiocentric lymphoma, Mucoepidermoid Carcinoma, NK/T-cell lymphoma, Malignant Mixed Tumors, Intestinal T-cell lymphoma, Adenocarcinoma, Malignant Mesothelioma, Fibrosarcoma, Sarcomotoid Type lung cancer, Osteosarcoma, Epithelial Type lung cancer, Chondrosarcoma, Melanoma, cancer of the gastrointestinal tract, olfactory Neuroblastoma, Squamous Cell Carcinoma, Isolated Plasmocytoma, Adenocarcinoma, Inverted Papillomas, Carcinoid, Undifferentiated Carcinoma, Malignant Melanoma, Mucoepidermoid Carcinoma, Adenocarcinoma, Acinic Cell Carcinoma, Gastric Carcinoma, Malignant Mixed Tumor, Gastric Lymphoma, Gastric Stromal Cell Tumors, Amenoblastoma, Lymphoma, Odontoma, Intestinal Stromal Cell tumors, thymus cancers, Malignant Thymoma, Carcinids, Type I (Invasive thymoma), Malignant Mesethelioma, Type II (Thymic carcinoma), Non-mucin producing adenocarcinoma, Squamous cell carcinoma, Lymph epithelioma, cancers of the liver and biliary tract, Squamous Cell Carcinoma, Hepatocellular Carcinoma, Adenocarcinoma, Cholangiocarcinoma, Hepatoblastoma, papillary cancer, Angiosarcoma, solid Bronchioalveolar cancer, Fibrolameller Carcinoma, Small Cell Carcinoma, Carcinoma of the Gallbladder, Intermediate Cell carcinaoma, Large Cell Carcinoma, Squamous Cell Carcinoma, Undifferentiated cancer, cancer of the pancreas, cancer of the female genital tract, Squamous Cell Carcinoma, Cystadenocarcinoma, Basal Cell Carcinoma, Insulinoma, Melanoma, Gastrinoma, Fibrosarcoma, Glucagonamoa, Intaepithelial Carcinoma, Adenocarcinoma Embryonal, cancer of the kidney, Rhabdomysarcoma, Renal Cell Carcinoma, Large Cell Carcinoma, Nephroblastoma (Wilm's tumor), Neuroendocrine or Oat Cell carcinoma, cancer of the lower urinary tract, Adenosquamous Carcinoma, Urothelial Tumors, Undifferentiated Carcinoma, Squamous Cell Carcinoma, Carcinoma of the female genital tract, Mixed Carcinoma, Adenoacanthoma, Sarcoma, Small Cell Carcinoma, Carcinosarcoma, Leiomyosarcoma, Endometrial Stromal Sarcoma, cancer of the male genital tract, Serous Cystadenocarcinoma, Mucinous Cystadenocarcinoma, Sarcinoma, Endometrioid Tumors, Speretocytic Sarcinoma, Embyonal Carcinoma, Celioblastoma, Choriocarcinoma, Teratoma, Clear Cell Carcinoma, Leydig Cell Tumor, Unclassified Carcinoma, Sertoli Cell Tumor, Granulosa-Theca Cell Tumor, Sertoli-Leydig Cell Tumor, Disgerminoma, Undifferentiated Prostatic Carcinoma, Teratoma, Ductal Transitional carcinoma, breast cancer, Phyllodes Tumor, cancer of the bones joints and soft tissue, Paget's Disease, Multiple Myeloma, Insitu Carcinoma, Malignant Lymphoma, Invasive Carcinoma, Chondrosacrcoma, Mesenchymal Chondrosarcoma, cancer of the endocrine system, Osteosarcoma, Adenoma, Ewing Tumor, endocrine Carcinoma, Malignant Giant Cell Tumor, Meningnoma, Adamantinoma, Cramiopharlingioma, Malignant Fibrous Histiocytoma, Papillary Carcinoma, Histiocytoma, Follicular Carcinoma, Desmoplastic Fibroma, Medullary Carcinoma, Fibrosarcoma, Anoplastic Carcinoma, Chordoma, Adenoma, Hemangioendothelioma, Memangispericytoma, Pheochromocytoma, Liposarcoma, Neuroblastoma, Paraganglioma, Histiocytoma, Pineal cancer, Rhabdomysarcoms, Pineoblastoma, Leiomyosarcoma, Pineocytoma, Angiosarcoma, skin cancer, cancer of the nervous system, Melanoma, Schwannoma, Squamous cell carcinoma, Neurofibroma, Basal cell carcinoma, Malignant Periferal Nerve Sheath Tumor, Merkel cell carcinoma, Sheath Tumor, Extramamary Paget's Disease, Astrocytoma, Paget's Disease of the nipple, Fibrillary Astrocytoma, Glioblastoma Multiforme, Brain Stem Glioma, Cutaneous T-cell lymphoma, Pilocytic Astrocytoma, Xanthorstrocytoma, Histiocytosis, Oligodendroglioma, Ependymoma, Gangliocytoma, Cerebral Neuroblastoma, Central Neurocytoma, Dysembryoplastic Neuroepithelial Tumor, Medulloblastoma, Malignant Meningioma, Primary Brain Lymphoma, Primary Brain Germ Cell Tumor, cancers of the eye, Squamous Cell Carcinoma, Mucoepidermoid Carcinoma, Melanoma, Retinoblastoma, Glioma, Meningioma, cancer of the heart, Myxoma, Fibroma, Lipoma, Papillary Fibroelastoma, Rhasdoyoma, or Angiosarcoma among others.

Diseases or conditions other than cancer for which stratified grades have been correlated with clinical outcome can also be used in a method of the disclosure to determine a prognostic model or to determine a prognosis for an individual suspected of having the disease or condition. Exemplary clinical outcomes that can be determined from a model of the disclosure include, for example, relapse probability, survival rate, or time to relapse. Another clinical outcome that can be determined from a model of the disclosure is response to a particular course of therapy such as surgical removal of a tumor, radiation, or chemotherapy.

In general, it is preferable to use signature genes for which the difference between the level of expression of the signature gene in prostate cancer cells or prostate-associated body fluids and the level of expression of the same signature gene in normal prostate cells or prostate-associated body fluids is as great as possible. Although the difference can be as small as the limit of detection of the method for assessing expression of the signature gene, it is preferred that the difference be at least greater than the standard error of the assessment method, and preferably a difference of at least 1.1-, 1.2-, 1.3-, 1.4-, 1.5-, 1.6-, 1.7-, 1.8-, 1.9-, 2-, 3-, 4-, 5-, 6-, 7-, 8-, 9-, 10-, 15-, 20-, 25-, 100-, 500-, 1000-fold or greater.

The skilled person will appreciate that patient tissue samples containing prostate cells or prostate cancer cells may be used in the methods of the present disclosure including, but not limited to those aimed at predicting relapse probability. In these embodiments, the level of expression of the signature gene can be assessed by assessing the amount, e.g. absolute amount or concentration, of a signature gene product, e.g., protein and RNA transcript encoded by the signature gene and fragments of the protein and RNA transcript) in a sample, e.g., stool and/or blood obtained from a patient. The sample can, of course, be subjected to a variety of well-known post-collection preparative and storage techniques (e.g. fixation, storage, freezing, lysis, homogenization, DNA or RNA extraction, ultrafiltration, concentration, evaporation, centrifugation, etc.) prior to assessing the amount of the signature gene product in the sample.

In the methods of the disclosure aimed at preparing a model for prostate cancer relapse prediction, it is understood that the particular clinical outcome associated with each sample contributing to the model must be known. Consequently, the model can be established using archived tissues. In the methods of the disclosure aimed at preparing a model for prostate cancer relapse prediction, total RNA is generally extracted from the source material of interest, generally an archived tissue such as a formalin-fixed, paraffin-embedded tissue, and subsequently purified. Methods for obtaining robust and reproducible gene expression patterns from archived tissues, including formalin-fixed, paraffin-embedded (FFPE) tissues are taught in United States Patent Publication 2004/0259105, which is incorporated herein by reference in its entirety. Commercial kits and protocols for RNA extraction from FFPE tissues are available including, for example, ROCHE High Pure RNA Paraffin Kit (Roche) MasterPure™ Complete DNA and RNA Purification Kit (EPICENTRE®Madison, Wis.); Paraffin Block RNA Isolation Kit (Ambion, Inc.) and Rneasy™ Mini kit (Qiagen, Chatsworth, Calif.).

The use of FFPE tissues as a source of RNA for RT-PCR has been described previously (Stanta et al., Biotechniques 11:304-308 (1991); Stanta et al., Methods Mol. Biol. 86:23-26 (1998); Jackson et al., Lancet 1:1391 (1989); Jackson et al., J. Clin. Pathol. 43:499-504 (1999); Finke et al., Biotechniques 14:448-453 (1993); Goldsworthy et al., Mol. Carcinog. 25:86-91 (1999); Stanta and Bonin, Biotechniques 24:271-276 (1998); Godfrey et al., J. Mol. Diagnostics 2:84 (2000); Specht et al., J. Mol. Med. 78:B27 (2000); Specht et al., Am. J. Pathol. 158:419-429 (2001)). For quick analysis of the RNA quality, RT-PCR can be performed utilizing a pair of primers targeting a short fragment in a highly expressed gene, for example, actin, ubiquitin, gapdh or other well-described commonly used housekeeping gene. If the cDNA synthesized from the RNA sample can be amplified using this pair of primers, then the sample is suitable for the a quantitative measurements of RNA target sequences by any method preferred, for example, the DASL assay, which requires only a short cDNA fragment for the annealing of query oligonucleotides.

There are numerous tissue banks and collections including exhaustive samples from all stages of a wide variety of disease states, most notably cancer. The ability to perform genotyping and/or gene expression analysis, including both qualitative and quantitative analysis on these samples enables the application of this methodology to the methods of the disclosure.

Tissue samples useful for preparing a model for prostate cancer relapse prediction include, for example, paraffin and polymer embedded samples, ethanol embedded samples and/or formalin and formaldehyde embedded tissues, although any suitable sample may be used. In general, nucleic acids isolated from archived samples can be highly degraded and the quality of nucleic preparation can depend on several factors, including the sample shelf life, fixation technique and isolation method. However, using the methodologies taught in United States Patent Publication 2004/0259105, which have the significant advantage that short or degraded targets can be used for analysis as long as the sequence is long enough to hybridize with the oligonucleotide probes, highly reproducible results can be obtained that closely mimic results found in fresh samples.

Archived tissue samples, which can be used for all methods of the disclosure, typically have been obtained from a source and preserved. Preferred methods of preservation include, but are not limited to paraffin embedding, ethanol fixation and formalin, including formaldehyde and other derivatives, fixation as are known in the art. A tissue sample may be temporally "old", e.g. months or years old, or recently fixed. For example, post-surgical procedures generally include a fixation step on excised tissue for histological analysis. In a preferred embodiment, the tissue sample is a diseased tissue sample, particularly a prostate cancer tissue, including primary and secondary tumor tissues as well as lymph node tissue and metastatic tissue.

Thus, an archived sample can be heterogeneous and encompass more than one cell or tissue type, for example, tumor and non-tumor tissue. Preferred tissue samples include solid tumor samples including, but not limited to, tumors of the prostate. It is understood that in applications of the present disclosure to conditions other than prostate cancer the tumor source can be brain, bone, heart, breast, ovaries, prostate, uterus, spleen, pancreas, liver, kidneys, bladder, stomach and muscle. Similarly, depending on the condition, suitable tissue samples include, but are not limited to, bodily fluids (including, but not limited to, blood, urine, serum, lymph, saliva, anal and vaginal secretions, perspiration and semen, of virtually any organism, with mammalian samples being preferred and human samples being particularly preferred). In embodiments directed to methods of establishing a model for relapse prediction, the tissue sample is one for which patient history and outcome is known. Generally, the disclosure methods can be practiced with the signature gene sequence contained in an archived sample or can be practiced with signature gene sequences that have been physically separated from the sample prior to performing a method of the disclosure.

If required, a nucleic acid sample having the signature gene sequence(s) are prepared using known techniques. For example, the sample can be treated to lyse the cells, using known lysis buffers, sonication, electroporation, etc., with purification and amplification as outlined below occurring as needed, as will be appreciated by those in the art. In addition, the reactions can be accomplished in a variety of ways, as will be appreciated by those in the art. Components of the reaction may be added simultaneously, or sequentially, in any order, with preferred embodiments outlined below. In addition, the reaction can include a variety of other reagents which can be useful in the assays. These include reagents like salts, buffers, neutral proteins, e.g. albumin, detergents, etc., which may be used to facilitate optimal hybridization and detection, and/or reduce non-specific or background interactions. Also reagents that otherwise improve the efficiency of the assay, such as protease inhibitors, nuclease inhibitors, anti-microbial agents, etc., can be used, depending on the sample preparation methods and purity.

In a preferred embodiment mRNA is isolated from paraffin embedded samples as is known in the art. Preferred methods include the use of the Paraffin Block RNA Isolation Kit by Ambion (Catalog number 1902, which instruction manual is incorporated herein by reference) or the high pure RNA parafin kit by Roche (cat #3270289). Samples of mRNA can be obtained from other samples using methods known in the art including for example, those described in Sambrook et al., Molecular Cloning: A Laboratory Manual, 3rd edition, Cold Spring Harbor Laboratory, New York (2001) or in Ausubel et al., Current Protocols in Molecular Biology, John Wiley and Sons, Baltimore, Md. (1998), or those that are commercially available such as the Invitrogen PureLink miRNA isolation kit (cat# K1570) or mRNA isolation kits from Ambion (Austin, Tex.). Once prepared, mRNA or other nucleic acids are analyzed by methods known to those of skill in the art. The nucleic acid sequence corresponding to a signature gene can be any length, with the understanding that longer sequences are more specific.

Recently developed methods for obtaining robust and reproducible gene expression patterns from archived tissues, including formalin-fixed, paraffin-embedded (FFPE) tissues as taught in United States Patent Application Publication No. 2004/0259105 have the significant advantage that short or degraded targets can be used for analysis as long as the sequence is long enough to hybridize with the oligonucleotide probes. Thus, even degraded target nucleic acids can be analyzed. Preferably a nucleic acid corresponding to a signature gene is at least 20 nucleotides in length. Preferred ranges are from 20 to 100 nucleotides in length, with from 30 to 60 nucleotides being more preferred and from 40 to 50 being most preferred.

In addition, when nucleic acids are to be detected preferred methods utilize cutting or shearing techniques to cut the nucleic acid sample containing the target sequence into a size that will facilitate handling and hybridization to the target. This can be accomplished by shearing the nucleic acid through mechanical forces (e.g. sonication) or by cleaving the nucleic acid using restriction endonucleases, or any other methods known in the art. However, in most cases, the natural degradation that occurs during archiving results in "short" oligonucleotides. In general, the methods of the disclosure can be done on oligonucleotides as short as 20-100 basepairs, with from 20 to 50 being preferred, and between 40 and 50, including 44, 45, 46, 47, 48 and 49 being the most preferred.

The disclosure also provides a collection of isolated probes specific for prostate cancer signature genes comprising at least two genes selected from the group consisting of NKX2-1, UPK1A, ADRA2C, ABCC11, MMP11, CPVL, ZYG11A, CLEC4F, OAS2, PGC, UPK3B, PCBP3, ABLIM1, EDARADD, GPR81, MYBPC1, F10, KCNA3, GLDC, KCNQ2, RAPGEF1, TUBB2B, MB, DUOXA1, C2orf43, DUOX1, PCA3 and NPR3. The disclosure also provides a collection of isolated probes specific for at least one gene selected from the group consisting of NKX2-1, UPK1A, ABCC11, MMP11, CPVL, ZYG11A, CLEC4F, OAS2, PGC, UPK3B, PCBP3, EDARADD, GPR81, MYBPC1, KCNA3, GLDC, KCNQ2, RAPGEF1, TUBB2B, MB, DUOXA1, C2orf43, DUOX1, and NPR3. The disclosure also provides a collection of isolated probes specific for prostate cancer signature genes comprising at least 2, 3, 4, 5, 6, 7, 8, or 9 genes selected from the group consisting of NKX2-1, UPK1A, ADRA2C, ABCC11, MMP11, CPVL, ZYG11A, CLEC4F, OAS2, and PGC. The disclosure also provides a collection of isolated probes specific for prostate cancer signature genes comprising at least 2, 3, 4, 5, 6, 7, 8, or 9 genes selected from the group consisting of ZYG11A, MMP11, MYBPC1, DUOX1, EDARADD, PGC, GPR81, NKX2-1, ABLIM1, and ABCC11.

The disclosure includes compositions, kits, and methods for assessing the probability of relapse of cancer for an individual from which a sample is obtained. The sample can be, for example, an archived tissue sample or a sample obtained from a patient. Where necessary, the compositions, kits, and methods are adapted for use with samples other than patient samples. For example, when the sample to be used is a parafinized, archived human tissue sample, it can be necessary to adjust the ratio of compounds in the compositions of the disclosure, in the kits of the disclosure, or the methods used to assess levels of gene expression in the sample. Such methods are well known in the art and within the skill of the ordinary artisan. A kit is any manufacture (e.g. a package or container) including at least one reagent, e.g. a probe, for specifically detecting the expression of a signature gene of the disclosure. The kit may be promoted, distributed, or sold as a unit for performing the methods of the present disclosure. It is recognized that the compositions, kits, and methods of the disclosure will be of particular utility to patients having a history of prostate cancer and their medical advisors.

The practice of the present disclosure employs, unless otherwise indicated, conventional techniques of molecular biology (including recombinant techniques), microbiology, cell biology, and biochemistry, which are within the skill of the art. Such techniques are explained in the literature, such as, "Molecular Cloning: A Laboratory Manual", Second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology", Fourth edition (D. M. Weir & C. C. Blackwell, eds., Blackwell Science Inc., 1987); "Gene Transfer Vectors for Mammalian Cells" (J. M. Miller & M. P. Calos, eds., 1987); "Current Protocols in Molecular Biology" (F. M. Ausubel et al., eds., 1987); and "PCR: The Polymerase Chain Reaction", (Mullis et al., eds., 1994).

Although the use of the 28 genes, and subsets thereof, has been exemplified with respect to prognosis and diagnosis methods utilizing expression levels of mRNA species produced by these genes, it will be understood that similar diagnostic and prognostic methods can utilize other measures such as methylation levels for the genes which can be correlated with expression levels or a measure of the level or activities of the protein products of the genes. Methylation can be determined using methods known in the art such as those set forth in U.S. Pat. No. 6,200,756 or US 2003/0170684, each of which is incorporated herein by reference. The level and activity of proteins can be determined using methods known in the art such as antibody detection techniques or enzymatic assays particular to the activity being evaluated. Furthermore, prognosis or diagnosis can be based on the presence of mutations or polymorphisms identified in the genes that affect expression of the gene or activity of the protein product.

Information relevant to the patient's diagnosis include, but are not limited to, age, ethnicity, serum PSA at the time of surgery, tumor localization, pertinent past medical history related to co-morbidity, other oncological history, family history for cancer, physical exam findings, radiological findings, biopsy date, biopsy result, types of operation performed (radical retropubic or radical perineal prostatectomy), TNM staging, neoadjuvant therapy (i.e. chemotherapy, hormones), adjuvant or salvage radiotherapy, hormonal therapy for a rising PSA (biochemical disease relapse), local vs. distant disease recurrence and survival outcome. These clinical variables may be included in the predictive model in various embodiments.

In some embodiments, biological samples in addition to or instead of prostate tissue may be used to determine the expression levels of the signature genes. In some embodiments, the suitable biological samples include, but are not limited to, circulating tumor cells (CTCs) isolated from the blood, urine of the patients or other body fluids, exosomes, and circulating tumor nucleic acids.

In some embodiments, the gene expression levels of the signature genes may be integrated with other biomarkers to predict the progression of PCa. Suitable biomarkers for this purpose include, but are not limited to, germline and somatic mutations, DNA methylation markers, and protein markers. In some embodiments, the combination of the signature genes and other biomarkers can be implemented by including both the signature genes and the biomarkers in the same predictive model. In some embodiments, the effect of the other biomarkers may be accounted for in a computational mechanism in addition to the predictive model, such as a second model that combines the output of the first predictive model with the effects of the other biomarkers. One skilled in the art understands various approaches may be used to combine the effects of the signature genes and biomarkers to predict the progression of PCa.

In some embodiments, the gene expression levels of the signature genes may be measured multiple times. In some embodiments, the dynamics of the expression levels may be used in combination of the signature genes' expression levels to better predict the clinical outcome. One skilled in the art understands various approaches may be used to combine the effects of the levels and the dynamics of the signature genes' expression to predict the progression of PCa.

Determining Gene Expression Level

The methods of the disclosure depend on the detection of differentially expressed genes for expression profiling across heterogeneous tissues. Thus, the methods depend on profiling genes whose expression in certain tissues is activated to a higher or lower level in an individual afflicted with a condition, for example, cancer, such as prostate cancer, relative to its expression in a non-cancerous tissues or in a control subject. Gene expression can be activated to a higher or lower level at different stages of the same conditions and a differentially expressed gene can be either activated or inhibited at the nucleic acid level or protein level, or may be subject to alternative splicing to result in a different polypeptide product. Such differences can be evidenced by a change in mRNA levels, surface expression, secretion or other partitioning of a polypeptide, for example. For the purpose of this disclosure, differential gene expression is considered to be present when there is at least about 1.1-fold, 1.2-fold, 1.3-fold, 1.4-fold, 1.5-fold, 1.6-fold, 1.7-fold, 1.8-fold, 1.9-fold, to two-fold.

Differential signature gene expression can be identified, or confirmed using methods known in the art such as qRT-PCR (quantitative reverse-transcription polymerase chain reaction) and microarray analysis. In particular embodiments, differential signature gene expression can be identified, or confirmed using microarray techniques. Thus, the signature genes can be measured in either fresh or paraffin-embedded tumor tissue, using microarray technology. In this method, polynucleotide sequences of interest are plated, or arrayed, on a microchip substrate. The arrayed sequences are then hybridized with specific DNA probes from cells or tissues of interest. In a preferred embodiment the technology combines fiber optic bundles and beads that self-assemble into an array. Each fiber optic bundle contains thousands to millions of individual fibers depending on the diameter of the bundle. Sensors are affixed to each bead in a given batch. The particular molecules on a bead define that bead's function as a sensor. To form an array, fiber optic bundles are dipped into pools of coated beads. The coated beads are drawn into the wells, one bead per well, on the end of each fiber in the bundle. The present disclosure is not limited to the solid supports described above. Indeed, a variety of other solid supports are contemplated including, but not limited to, glass microscope slides, glass wafers, gold, silicon, microchips, and other plastic, metal, ceramic, or biological surfaces. Microarray analysis can be performed by commercially available equipment, following manufacturer's protocols, such as by using Illumina's technology.

Exemplary arrays that are useful include, without limitation, a Sentrix® Array or Sentrix® BeadChip Array available from Illumina®, Inc. (San Diego, Calif.) or others including beads in wells such as those described in U.S. Pat. Nos. 6,266,459, 6,355,431, 6,770,441, and 6,859,570; and PCT Publication No. WO 00/63437, each of which is hereby incorporated by reference. Other arrays having particles on a surface include those set forth in US 2005/0227252; US 2006/0023310; US 2006/006327; US 2006/0071075; US 2006/0119913; U.S. Pat. Nos. 6,489,606; 7,106,513; 7,126,755; 7,164,533; WO 05/033681; and WO 04/024328, each of which is hereby incorporated by reference.

An array of beads useful in the disclosure can also be in a fluid format such as a fluid stream of a flow cytometer or similar device. Exemplary formats that can be used in the disclosure to distinguish beads in a fluid sample using microfluidic devices are described, for example, in U.S. Pat. No. 6,524,793. Commercially available fluid formats for distinguishing beads include, for example, those used in XMAP™ technologies from Luminex or MPSS™ methods from Lynx Therapeutics.

Further examples of commercially available microarrays that can be used in the disclosure include, for example, an Affymetrix® GeneChip® microarray or other microarray synthesized in accordance with techniques sometimes referred to as VLSIPS™ (Very Large Scale Immobilized Polymer Synthesis) technologies as described, for example, in U.S. Pat. Nos. 5,324,633; 5,744,305; 5,451,683; 5,482,867; 5,491,074; 5,624,711; 5,795,716; 5,831,070; 5,856,101; 5,858,659; 5,874,219; 5,968,740; 5,974,164; 5,981,185; 5,981,956; 6,025,601; 6,033,860; 6,090,555; 6,136,269; 6,022,963; 6,083,697; 6,291,183; 6,309,831; 6,416,949; 6,428,752 and 6,482,591, each of which is hereby incorporated by reference.

A spotted microarray can also be used in a method of the disclosure. An exemplary spotted microarray is a CodeLink™ Array available from Amersham Biosciences. Another microarray that is useful in the disclosure is one that is manufactured using inkjet printing methods such as SurePrint™ Technology available from Agilent Technologies. Other microarrays that can be used in the disclosure include, without limitation, those described in Butte, Nature Reviews Drug Discov. 1:951-60 (2002) or U.S. Pat. Nos. 5,429,807; 5,436,327; 5,561,071; 5,583,211; 5,658,734; 5,837,858; 5,919,523; 6,287,768; 6,287,776; 6,288,220; 6,297,006; 6,291,193; and 6,514,751; and WO 93/17126; WO 95/35505, each of which is hereby incorporated by reference.

DASL can be used for quantitative measurements of RNA target sequences as well as for DNA target sequences. DASL is described, for example, in Fan et al., Genome Res. 14:878-85 (2004); US 2003/0108900 and US 2004/0259105, each of which is incorporated herein by reference. Notably, the sensitivity of DASL using RNA from paraffin samples is about 80% compared to the assay using RNA prepared from fresh frozen samples, with results up to 90% sensitivity observed. Gene expression can be monitored and compared in formalin-fixed, paraffin-embedded clinical samples archived for more than 5 years.

The expression patterns for signature genes are determined based on quantitative detection of nucleic acids or oligonucleotides corresponding to the signature genes, which means at least two nucleotides covalently linked together. Thus, the disclosure also provides a collection of nucleic acids and oligonucleotides that correspond to a signature gene or a set of signature genes. A nucleic acid useful in the methods of the disclosure will generally contain phosphodiester bonds, although in some cases, nucleic acid analogs are included that may have alternate backbones, including, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169-176). Several nucleic acid analogs are described in Rawls, C & E News Jun. 2, 1997 page 35. Modifications of the ribose-phosphate backbone may be done to facilitate the addition of labels, or to increase the stability and half-life of such molecules in physiological environments. Nucleic acid analogs can find use in the methods of the disclosure as well as mixtures of naturally occurring nucleic acids and analogs.

The nucleic acids corresponding to signature genes can be single stranded or double stranded, as specified, or contain portions of both double stranded or single stranded sequence. The nucleic acid can be DNA, both genomic and cDNA, RNA or a hybrid, where the nucleic acid contains any combination of deoxyribo- and ribo-nucleotides, and any combination of bases, including, for example, uracil, adenine, thymine, cytosine, guanine, inosine, xanthine hypoxanthine, isocytosine, isoguanine. A nucleic acid sequence corresponding to a signature gene can be a portion of the gene, a regulatory sequence, genomic DNA, cDNA, RNA including mRNA and rRNA, or others.

A nucleic acid sequence corresponding to a signature gene can be derived from the tissue sample, or from a secondary source such as a product of a reaction such as, for example, a detection sequence from an invasive cleavage reaction, a ligated probe from an OLA or DASL reaction, an extended probe from a PCR reaction, or PCR amplification product, ("amplicon"). Exemplary methods for preparing secondary probes from target sequences are described in US 2003/0108900; US 2003/0170684; US 2003/0215821; US 2004/0121364; and US 2005/0181394. Thus, a nucleic acid sequence corresponding to a signature gene can be derived from the primary or from a secondary source of nucleic acid.

As will be appreciated by those in the art, a complementary nucleic acid sequence useful in the methods of the disclosure can take many forms and probes are made to hybridize to nucleic acid sequences to determine the presence or absence of the signature gene in a sample. In a preferred embodiment, a plurality of nucleic acid sequences is detected. As used herein, "plurality" or grammatical equivalents herein refers to at least 2, 10, 20, 25, 50, 100 or 200 different nucleic sequences, while at least 500 different nucleic sequences is preferred. More preferred is at least 1000, with more than 5000 or 10,000 particularly preferred and more than 50,000 or 100,000 most preferred. Detection can be performed on a variety of platforms such as those set forth above or in the Examples.

The expression level of a signature gene in a tissue sample can be determined by contacting nucleic acid molecules derived from the tissue sample with a set of probes under conditions where perfectly complementary probes form a hybridization complex with the nucleic acid sequences corresponding to the signature genes, each of the probes including at least two universal priming sites and a signature gene target-specific sequence; amplifying the probes forming the hybridization complexes to produce amplicons; and detecting the amplicons, wherein the detection of the amplicons indicates the presence of the nucleic acid sequences corresponding to the signature gene in the tissue sample; and determining the expression level of the signature gene.

In the context of the present disclosure, multiplexing refers to the detection, analysis or amplification of a plurality of nucleic acid sequences corresponding to the signature genes. In one embodiment multiplex refers to the number of nucleic acid sequences corresponding to a signature gene to be analyzed in a single reaction, vessel or step. The multiplexing method is useful for detection of a single nucleic acid sequence corresponding to a signature gene as well as a plurality of nucleic acid sequences corresponding to a set of signature genes. In addition, as described below, the methods of the disclosure can be performed simultaneously and in parallel in a large number of tissue samples.

The expression level of nucleic acid sequences corresponding to a set of signature genes in a tissue sample can be determined by contacting nucleic acid molecules derived from the tissue sample with a set of probes under conditions where complementary probes form a hybridization complex with the signature gene-specific nucleic acid sequences, each of the probes including at least two universal priming sites and a signature gene-specific nucleic acid sequence; amplifying the probes forming the hybridization complexes to produce amplicons; detecting the amplicons, wherein the detection of the amplicons indicates the presence of the nucleic acid sequences corresponding to the set of signature genes in the tissue sample; and determining the expression level of the target sequences, wherein the expression of at least two, at least three, at least five signature gene-specific sequences is detected.

The presence of one, two or a plurality of nucleic acid sequences corresponding to a set of signature genes can be determined in a tissue sample using single, double or multiple probe configurations. The methods of the disclosure can be practiced with tissue samples having substantially degraded nucleic acids. Although methods for pre-qualifying samples with respect to nucleic acid degradation are described above, those skilled in the art will recognize that other detection methods described herein or known in the art can be used to detect RNA levels in a sample suspected of having degraded nucleic acids, thereby determine the level of nucleic acid degradation in accordance with the disclosure.

The present disclosure particularly draws on methodologies outlined in US 2003/0215821; US 2004/0018491; US 2003/0036064; US 2003/0211489, each of which is expressly incorporated by reference in their entirety. In addition, universal priming methods are described in detail in US 2002/0006617; US 2002/0132241, each of which is expressly incorporated herein by reference. In addition, multiplex methods are described in detail US 2003/0211489; US 2003/0108900, each of which is expressly incorporated herein by reference. In general, the methods of the disclosure can be performed in a variety of ways, as further described below and in the cited applications incorporated by reference. For example, mRNA signature samples can initially be subjected to a "complexity reduction" step, whereby the presence of a particular target is confirmed by adding probes that are enzymatically modified in the presence of the signature gene-specific nucleic acid sequence. The modified probes are then amplified and detected in a wide variety of ways. Preferred embodiments draw on multiplexing methods, which allow for the simultaneous detection of a number of nucleic acid sequences, for example, corresponding to a set of signature genes, as well as multiplexing amplification reactions, for example by using universal priming sequences to do multiplex PCR reactions. If desired, the initial step also can be both a complexity reduction and an amplification step.

The randomly ordered BeadArray™ technology (Michael et al., *Anal Chem* 70, 1242-8 (1998); Walt, *Science* 287, 451-2 (2000)) has been developed at Illumina as a platform for SNP genotyping (Fan et al., *Cold Spring Harb Symp Quant Biol* 68:69-78 (2003); Gunderson et al., *Nat Genet* 37:549-54 (2005)), gene expression profiling (Bibikova et al. *Am J Pathol* 165:1799-807 (2004); Fan et al., *Genome Res* 14:878-85 (2004); Kuhn et al., *Genome Res* 14:2347-56 (2004); Yeakley et al., *Nat Biotechnol* 20:353-8 (2002)) and DNA methylation detection (Bibikova et al., *Genome Res* 16:383-93 (2006)). Each array was assembled on an optical fiber bundle consisting of about 50,000 individual fibers fused together into a hexagonally packed matrix. The ends of the bundle were polished, and one end was chemically etched to create a microscopic well in each fiber. These wells were each filled with a 3-micron diameter silica bead. Each derivatized bead had several hundred thousand copies of a particular oligonucleotide covalently attached and available for hybridization. Bead libraries were prepared by conjugation of oligonucleotides to silica beads, followed by quantitative pooling together of the individual bead types. Because the beads were positioned randomly on the array, a decoding process was carried out to determine the location and identity of each bead in every array location (Gunderson et al., *Genome Res* 14:870-7 (2004)). Each of the 1,624 bead types in the resulting universal array was present at an average redundancy of about 30. Consequently, each assay measurement was the result of data averaged from multiple beads, which increased precision and greatly reduced the possibility of error.

To further increase sample throughput, the arrays were formatted into a matrix, in a pattern that matched the wells of standard 96-well microtiter plates. The matrix format allows streamlined sample handling. By bringing the array to the sample (literally dipping it into the microtiter well), sample and array processing is simplified and integrated for handling of 96 separate samples simultaneously.

A flexible, sensitive, accurate and cost-effective gene expression profiling assay, the DASL (for DNA-mediated annealing, selection, extension and ligation) assay, can be used for parallel analysis of thousands of sequence targets. In this assay in one embodiment, two oligos were designed to target a specific gene sequence. Total RNA was first converted to cDNA by random priming. The corresponding query oligos hybridized to the cDNA, and were extended and ligated enzymatically. The ligated products were then amplified and fluorescently labeled during PCR, and finally detected by binding to address sequences on the universal array. The hybridization intensity was used as a measurement of the original mRNA abundance in the sample.

Unlike most of the other array technologies that use an in vitro transcription (IVT)-mediated sample labeling procedure (Phillips and Eberwine, *Methods* 10, 283-8 (1996)), DASL uses random priming in the cDNA synthesis, and therefore does not depend on an intact poly-A tail for T7-oligo-d(T) priming. In addition, the assay utilizes a relatively short target sequence of about 50 nucleotides for query oligonucleotide annealing, thus allowing microarray analyses of degraded RNAs (Bibikova et al., *Am J Pathol* 165:1799-807 (2004); Bibikova et al., *Clin Chem* 50:2384-6 (2004))

Software developed at Illumina can be used for automatic image registration (Galinsky, *Bioinformatics* 19:1832-6 (2003)) and extraction of feature intensities. Briefly, the feature extraction algorithm represents a weighted 6×6 average of pixel intensities. The outlier algorithm was implemented at the feature level (each probe sequence was represented by 30 features on average) to remove features that fell outside of a robust confidence interval of the median response. Array data can be normalized using the "rank invariant" method in Illumina's BeadStudio software.

Apparatus and Systems for Predicting Progression of PCa

Analysis of the sequencing data and the diagnosis derived therefrom are typically performed using various computer executed algorithms and programs. Therefore, certain embodiments employ processes involving data stored in or transferred through one or more computer systems or other processing systems. Embodiments disclosed herein also relate to apparatus for performing these operations. This apparatus may be specially constructed for the required purposes, or it may be a general-purpose computer (or a group of computers) selectively activated or reconfigured by a computer program and/or data structure stored in the computer. In some embodiments, a group of processors performs some or all of the recited analytical operations collaboratively (e.g., via a network or cloud computing) and/or in parallel. A processor or group of processors for performing the methods described herein may be of various types including microcontrollers and microprocessors such as programmable devices (e.g., CPLDs and FPGAs) and non-programmable devices such as gate array ASICs or general purpose microprocessors.

In addition, certain embodiments relate to tangible and/or non-transitory computer readable media or computer program products that include program instructions and/or data (including data structures) for performing various computer-implemented operations. Examples of computer-readable media include, but are not limited to, semiconductor memory devices, magnetic media such as disk drives, magnetic tape, optical media such as CDs, magneto-optical media, and hardware devices that are specially configured to store and perform program instructions, such as read-only memory devices (ROM) and random access memory (RAM). The computer readable media may be directly controlled by an end user or the media may be indirectly controlled by the end user. Examples of directly controlled media include the media located at a user facility and/or media that are not shared with other entities. Examples of indirectly controlled media include media that is indirectly accessible to the user via an external network and/or via a service providing shared resources such as the "cloud." Examples of program instructions include both machine code, such as produced by a compiler, and files containing higher level code that may be executed by the computer using an interpreter.

In various embodiments, the data or information employed in the disclosed methods and apparatus is provided in an electronic format. Such data or information may include reads and tags derived from a nucleic acid sample, counts or densities of such tags that align with particular regions of a reference sequence (e.g., that align to a chromosome or chromosome segment), reference sequences (including reference sequences providing solely or primarily polymorphisms), counseling recommendations, diagnoses, and the like. As used herein, data or other information provided in electronic format is available for storage on a machine and transmission between machines. Conventionally, data in electronic format is provided digitally and may be stored as bits and/or bytes in various data structures, lists, databases, etc. The data may be embodied electronically, optically, etc.

In some embodiments, the disclosure provides A system for predicting progression of prostate cancer in an individual, the system comprising: an apparatus configured to determine expression levels of nucleic acids from a biological sample taken from the individual; and hardware logic designed or configured to perform operations comprising: (a) receiving expression levels of a collection of signature genes from a biological sample taken from said individual, wherein said collection of signature genes comprises at least two genes selected from the group consisting of: NKX2-1, UPK1A, ADRA2C, ABCC11, MMP11, CPVL, ZYG11A, CLEC4F, OAS2, PGC, UPK3B, PCBP3, ABLIM1, EDARADD, GPR81, MYBPC1, F10, KCNA3, GLDC, KCNQ2, RAPGEF1, TUBB2B, MB, DUOXA1, C2orf43, DUOX1, PCA3 and NPR3; (b) applying the expression levels to a predictive model relating expression levels of said collection of signature genes with prostate cancer progression; and (c) evaluating an output of said predictive model to predict progression of prostate cancer in said individual. In some embodiments, said collection of signature genes comprises at least one gene selected from the group consisting of: NKX2-1, UPK1A, ABCC11, MMP11, CPVL, ZYG11A, CLEC4F, OAS2, PGC, UPK3B, PCBP3, EDARADD, GPR81, MYBPC1, KCNA3, GLDC, KCNQ2, RAPGEF1, TUBB2B, MB, DUOXA1, C2orf43, DUOX1, and NPR3. In some embodiments, said collection of signature genes comprises at least two genes selected from the group consisting essentially of: NKX2-1, UPK1A, ADRA2C, ABCC11, MMP11, CPVL, ZYG11A, CLEC4F, OAS2, and PGC. In some embodiments, said collection of signature genes comprises at least two genes selected from the group consisting essentially of: ZYG11A, MMP11, MYBPC1, DUOX1, EDARADD, PGC, GPR81, NKX2-1, ABLIM1, and ABCC11.

In some embodiments, the apparatus of the system includes a microarray. In some embodiments, the apparatus includes a next generation sequencer. In some embodiments, the apparatus includes a qPCR device.

Sequencing Methods

In various embodiments, determination of gene expression levels may involve sequencing nucleic acids corresponding to genes of interests. Any of a number of sequencing technologies can be utilized.

Some sequencing technologies are available commercially, such as the sequencing-by-hybridization platform from Affymetrix Inc. (Sunnyvale, Calif.) and the sequencing-by-synthesis platforms from 454 Life Sciences (Bradford, Conn.), Illumina/Solexa (Hayward, Calif.) and Helicos Biosciences (Cambridge, Mass.), and the sequencing-by-ligation platform from Applied Biosystems (Foster City, Calif.), as described below. In addition to the single molecule sequencing performed using sequencing-by-synthesis of Helicos Biosciences, other single molecule sequencing technologies include, but are not limited to, the SMRT™ technology of Pacific Biosciences, the ION TORRENT™ technology, and nanopore sequencing developed for example, by Oxford Nanopore Technologies.

While the automated Sanger method is considered as a 'first generation' technology, Sanger sequencing including the automated Sanger sequencing, can also be employed in the methods described herein. Additional suitable sequencing methods include, but are not limited to nucleic acid imaging technologies, e.g., atomic force microscopy (AFM) or transmission electron microscopy (TEM). Illustrative sequencing technologies are described in greater detail below.

In one illustrative, but non-limiting, embodiment, the methods described herein comprise obtaining sequence information for the nucleic acids in a test sample from a subject being screened for a cancer, and the like, using single molecule sequencing technology of the Helicos True Single Molecule Sequencing (tSMS) technology (e.g. as described in Harris T. D. et al., Science 320:106-109 [2008]). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. In certain embodiments the templates can be at a density of about 100 million templates/cm2. The flow cell is then loaded into an instrument, e.g., HeliScope™ sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are discerned by imaging the flow cell surface. After imaging, a cleavage step removes the fluorescent label, and the process is repeated with other fluorescently labeled nucleotides until the desired read length is achieved. Sequence information is collected with each nucleotide addition step. Whole genome sequencing by single molecule sequencing technologies excludes or typically obviates PCR-based amplification in the preparation of the sequencing libraries, and the methods allow for direct measurement of the sample, rather than measurement of copies of that sample.

In another illustrative, but non-limiting embodiment, the methods described herein comprise obtaining sequence information for the nucleic acids in the test sample using the 454 sequencing (Roche) (e.g. as described in Margulies, M. et al. Nature 437:376-380 [2005]). 454 sequencing typically involves two steps. In the first step, DNA is sheared into fragments of approximately 300-800 base pairs, and the fragments are blunt-ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (e.g., picoliter-sized wells). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is measured and analyzed.

In another illustrative, but non-limiting, embodiment, the methods described herein comprises obtaining sequence information for the nucleic acids in the test sample using the SOLiD™ technology (Applied Biosystems). In SOLiD™ sequencing-by-ligation, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

In another illustrative, but non-limiting, embodiment, the methods described herein comprise obtaining sequence information for the nucleic acids in the test sample using the single molecule, real-time (SMRT™) sequencing technology of Pacific Biosciences. In SMRT sequencing, the continuous incorporation of dye-labeled nucleotides is imaged during DNA synthesis. Single DNA polymerase molecules are attached to the bottom surface of individual zero-mode wavelength detectors (ZMW detectors) that obtain sequence information while phospholinked nucleotides are being incorporated into the growing primer strand. A ZMW detector comprises a confinement structure that enables observation of incorporation of a single nucleotide by DNA polymerase against a background of fluorescent nucleotides that rapidly diffuse in an out of the ZMW (e.g., in microseconds). It typically takes several milliseconds to incorporate a nucleotide into a growing strand. During this time, the fluorescent label is excited and produces a fluorescent signal, and the fluorescent tag is cleaved off. Measurement of the corresponding fluorescence of the dye indicates which base was incorporated. The process is repeated to provide a sequence.

In another illustrative, but non-limiting embodiment, the methods described herein comprise obtaining sequence information for the nucleic acids in the test sample, e.g., DNA in a subject being screened for a cancer, and the like, using nanopore sequencing (e.g. as described in Soni G V and Meller A. Clin Chem 53: 1996-2001 [2007]). Nanopore sequencing DNA analysis techniques are developed by a number of companies, including, for example, Oxford Nanopore Technologies (Oxford, United Kingdom), Sequenom, NABsys, and the like. Nanopore sequencing is a single-molecule sequencing technology whereby a single molecule of DNA is sequenced directly as it passes through a nanopore. A nanopore is a small hole, typically of the order of 1 nanometer in diameter. Immersion of a nanopore in a conducting fluid and application of a potential (voltage) across it results in a slight electrical current due to conduction of ions through the nanopore. The amount of current that flows is sensitive to the size and shape of the nanopore. As a DNA molecule passes through a nanopore, each nucleotide on the DNA molecule obstructs the nanopore to a different degree, changing the magnitude of the current through the nanopore in different degrees. Thus, this change in the current as the DNA molecule passes through the nanopore provides a read of the DNA sequence.

In another illustrative, but non-limiting, embodiment, the methods described herein comprises obtaining sequence information for the nucleic acids in the test sample, e.g., DNA in a subject being screened for a cancer, and the like, using the chemical-sensitive field effect transistor (chemFET) array (e.g., as described in U.S. Patent Application Publication No. 2009/0026082). In one example of this technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be discerned as a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

In another embodiment, the present method comprises obtaining sequence information for the nucleic acids in the test sample using the Halcyon Molecular's technology, which uses transmission electron microscopy (TEM). The method, termed Individual Molecule Placement Rapid Nano Transfer (IMPRNT), comprises utilizing single atom resolution transmission electron microscope imaging of high-molecular weight (150 kb or greater) DNA selectively labeled with heavy atom markers and arranging these molecules on ultra-thin films in ultra-dense (3 nm strand-to-strand) parallel arrays with consistent base-to-base spacing. The electron microscope is used to image the molecules on the films to determine the position of the heavy atom markers and to extract base sequence information from the DNA. The method is further described in PCT patent publication WO 2009/046445. The method allows for sequencing complete human genomes in less than ten minutes.

In another embodiment, the DNA sequencing technology is the Ion Torrent single molecule sequencing, which pairs semiconductor technology with a simple sequencing chemistry to directly translate chemically encoded information (A, C, G, T) into digital information (0, 1) on a semiconductor chip. In nature, when a nucleotide is incorporated into a strand of DNA by a polymerase, a hydrogen ion is released as a byproduct. Ion Torrent uses a high-density array of micro-machined wells to perform this biochemical process in a massively parallel way. Each well holds a different DNA molecule. Beneath the wells is an ion-sensitive layer and beneath that an ion sensor. When a nucleotide, for example a C, is added to a DNA template and is then incorporated into a strand of DNA, a hydrogen ion will be released. The charge from that ion will change the pH of the solution, which can be detected by Ion Torrent's ion sensor. The sequencer—essentially the world's smallest solid-state pH meter—calls the base, going directly from chemical information to digital information. The Ion personal Genome Machine (PGM™) sequencer then sequentially floods the chip with one nucleotide after another. If the next nucleotide that floods the chip is not a match. No voltage change will be recorded and no base will be called. If there are two identical bases on the DNA strand, the voltage will be double, and the chip will record two identical bases called. Direct detection allows recordation of nucleotide incorporation in seconds.

In another embodiment, the present method comprises obtaining sequence information for the nucleic acids in the test sample using sequencing by hybridization. Sequencing-by-hybridization comprises contacting the plurality of polynucleotide sequences with a plurality of polynucleotide probes, wherein each of the plurality of polynucleotide probes can be optionally tethered to a substrate. The substrate might be flat surface comprising an array of known nucleotide sequences. The pattern of hybridization to the array can be used to determine the polynucleotide sequences present in the sample. In other embodiments, each probe is tethered to a bead, e.g., a magnetic bead or the like. Hybridization to the beads can be determined and used to identify the plurality of polynucleotide sequences within the sample.

In another embodiment, the present method comprises obtaining sequence information for the nucleic acids in the test sample by massively parallel sequencing of millions of DNA fragments using Illumina's sequencing-by-synthesis and reversible terminator-based sequencing chemistry (e.g. as described in Bentley et al., Nature 6:53-59 [2009]). Illumina's sequencing technology relies on the attachment of fragmented genomic DNA to a planar, optically transparent surface on which oligonucleotide anchors are bound. Template DNA is end-repaired to generate 5'-phosphorylated blunt ends, and the polymerase activity of Klenow fragment is used to add a single A base to the 3' end of the blunt phosphorylated DNA fragments. This addition prepares the DNA fragments for ligation to oligonucleotide adapters, which have an overhang of a single T base at their 3' end to increase ligation efficiency. The adapter oligonucleotides are complementary to the flow-cell anchors. Under limiting-dilution conditions, adapter-modified, single-stranded template DNA is added to the flow cell and immobilized by hybridization to the anchors. Attached DNA fragments are extended and bridge amplified to create an ultra-high density sequencing flow cell with hundreds of millions of clusters, each containing ~1,000 copies of the same template. In one embodiment, the randomly fragmented genomic DNA is amplified using PCR before it is subjected to cluster amplification. Alternatively, an amplification-free genomic library preparation is used, and the randomly fragmented genomic DNA is enriched using the cluster amplification alone (Kozarewa et al., Nature Methods 6:291-295 [2009]). The templates are sequenced using a robust four-color DNA sequencing-by-synthesis technology that employs reversible terminators with removable fluorescent dyes. High-sensitivity fluorescence detection is achieved using laser excitation and total internal reflection optics. Short sequence reads of about 20-40 bp, e.g., 36 bp, are aligned against a repeat-masked reference genome and unique mapping of the short sequence reads to the reference genome are identified using specially developed data analysis pipeline software. Non-repeat-masked reference genomes can also be used. Whether repeat-masked or non-repeat-masked reference genomes are used, only reads that map uniquely to the reference genome are counted. After completion of the first read, the templates can be regenerated in situ to enable a second read from the opposite end of the fragments. Thus, either single-end or paired end sequencing of the DNA fragments can be used. Partial sequencing of DNA fragments present in the sample is performed, and sequence tags comprising reads of predetermined length, e.g., 36 bp, are mapped to a known reference genome are counted. In one embodiment, the reference genome sequence is the NCBI36/hg18 sequence, which is available on the world wide web at genome.ucsc.edu/cgi-bin/hgGateway?org=Human&db=hg18&hgsid=166260105). Alternatively, the reference genome sequence is the GRCh37/hg19, which is available on the world wide web at genome.ucsc.edu/cgi-bin/hgGateway. Other sources of public sequence information include GenBank, dbEST, dbSTS, EMBL (the European Molecular Biology Laboratory), and the DDBJ (the DNA Databank of Japan). A number of computer algorithms are available for aligning sequences, including without limitation BLAST (Altschul et al., 1990), BLITZ (MPsrch) (Sturrock & Collins, 1993), FASTA (Person & Lipman, 1988), BOWTIE (Langmead et al., Genome Biology 10:R25.1-R25.10 [2009]), or ELAND (Illumina, Inc., San Diego, Calif., USA).

It is understood that modifications which do not substantially affect the activity of the various embodiments of this disclosure are also included within the definition of the disclosure provided herein. Accordingly, the following examples are intended to illustrate but not limit the present disclosure.

EXAMPLE

Methods

Patient Selection

All patients enrolled in this example were clinically-free of disease at the end of the surgery. Patients are followed every 4-6 months in year 1, every 6 months in years 2-3 and yearly thereafter. At each visit patients receive a physical examination, PSA measurement, and a chest x-ray. Clinical outcomes were measured by time to PSA and/or clinical recurrence and overall survival. PSA recurrence was defined as a rise in PSA above the undetectable ultrasensitive level as detected by two consecutive confirmatory values (1988-1994: PSA≥0.3 ng/ml; 1995-2005: PSA≥0.05 ng/ml; 2006-present: PSA≥0.03 ng/ml). The following baseline variables have been recorded for each patient: preoperative PSA (<4, 4-10, 11-20, >20), Gleason's score based on the surgical specimen (2-4, 5-6, 7, 8-10), pT-stage, pN-stage, and whether or not hormone therapy was given prior or post-surgery. In addition, data on other clinical features are available such as results of CT scans and bone scan evaluations, number of positive cores on biopsy, seminal vesicle involvement, percent of tumor involvement, Ki67 staining, and AR status.

All specimens from radical prostatectomies were assessed using consistent pathological reporting, and follow-up at the institution was standardized (clinical examinations and PSA measurements). Follow-up of patients were completed through routine perusal of patient medical records and physician notes. When necessary, phone calls were made to the patients or the patient's physician if there was a change in physician. Patients who underwent a radical prostatectomy from 1972 to 2009 were entered into the Institutional Review Board approved database maintained by the USC Institute of Urology. Last follow-up of patients was completed in May 2010.

This example included 293 patients with organ confined PCa (stage pT2) who underwent radical prostatectomy at the University of Southern California. Among these patients, 154 experienced no recurrence following radical prostatectomy, or had "No evidence of disease (NED)", 106 patients only had biochemical recurrence (BCR), and 33 patients had clinical recurrence, or metastasis of disease (CR).

Experimental Design

To develop a predictive model, a nested case-control was used. Cases are patients who were documented to have biochemical (PSA) recurrence after surgery in their medical records. Controls were selected using an incidence density sampling method. Controls were individuals who were randomly selected from the "risk set", or the recurrence-free patients still under follow-up at the time of the case's biochemical recurrence and still at risk of experiencing recurrence. Controls were matched to cases on operation year, pathologic Gleason and stage. Gleason score was relaxed in order to obtain eligible controls for each case by using categories of ≤6, 7, 8-10. Even though cases and controls were matched on BCR status, the primary clinical endpoint for this example was clinical recurrence, which was defined as either palpable local disease proven on biopsy or distant recurrence confirmed by imaging studies including MRCI, CT, bone scan or chest x-ray. For analyses that used CR as outcome the predictive models are developed by comparing CR patients to NED patients.

Identification of Malignant Glands for Microdissection

Prostate tissue for selected participants in this example was reviewed for the hematoxylin and eosin (H&E) stained slides of each tissue block and determined the best tissue block to use for microdissection, one with sufficient tumor tissue available that is also the most representative of the highest Gleason grade of the index tumor. Pathology technicians used a microtome to cut 10, 5-micron sections of the selected block, along with a cover-slipped H&E slide for clear visualization of the location of the tumor under the microscope. An experimenter clearly marked the location of tumor on each H&E slide of the corresponding block in order to use as a guide during microdissection of the tumor on the other non-cover-slipped slides.

Laser-Captured Microdissection of FFPE Tumors

In order to enrich for malignant glands and avoid contamination with stromal tissue or non-malignant glands, a laser capture microdissection (LCM) microscope (Arcturus® Laser Capture Microdissection, Model Veritas; Applied Biosystems by Life Technologies, Foster City, Calif.) was used to microdissect malignant prostate glands. For this purpose, slides obtained from the pathology core were de-paraffinized and lightly stained with H&E (no coverslip mounted) prior to microdissection. Appropriate measures were taken to insure reduced contamination of tissue and minimized loss of RNA in the tissue (e.g. proper use of lab coats and gloves, use of RNase-free reagents, and routine cleaning of equipment).

Isolation of RNA from Microdissected Prostate Cells

After obtaining tissue on the caps from the laser capture microdissection (approximately 4 LCM caps of tissue per case and 4-8, 5 micron slides depending on size of tumor area; 3-4 hours per case), the caps with the tissue of interest were suspended in 150 µL of tissue lysis buffer (Buffer PKD, provided by Qiagen) and 10 µL of Proteinase K in a 0.5 mL tube and temporarily stored at 4° C. until further RNA extraction (as seen in FIG. 3.3B). RNA extractions were completed using the Qiagen ALLPREP® DNA/RNA FFPE kit to have the option of recovering both RNA and DNA from the microdissected tissue (partial extracted DNA samples were stored in −20° C. for full extraction at a later time). The samples were vortexed then incubated at 56° C. for 15 minutes, placed on ice for 3 minutes, and centrifuged at full speed for 15 minutes to separate DNA and RNA. Subsequent steps of sample processing were performed according to the Kit manual. The samples were quantified using a Nanodrop machine. The isolated RNA samples were stored at 20 ng/uL in RNase-free water at −80° C.

Gene Expression Biomarkers

The Whole-Genome DASL HT assay (Illumina) was used to analyze over 29,000 sequence targets. Each target gene sequence was hybridized to the HumanHT-12 v4 BeadChip (Illumina; Whole-Genome DASL® HT Assay for Expression Profiling in FFPE Samples; Data Sheet: RNA Analysis, 2010). The HumanHT-12 v4 BeadChip, which efficiently processes 12 samples per BeadChip array, was used to detect the following transcripts using the RNA from the tumor samples: 27,253 coding transcripts (well-established annotations), 426 coding transcripts (provisional annotations), 1,580 non-coding transcripts (well-established annotations), and 26 non-coding transcripts (provisional annotations). Researchers used between 50-200 ng from each tumor to obtain profiles with the DASL platform. Cases and controls were run in pairs on the same chip. For quality control purposes, 20% of samples were included as duplicates.

Preprocessing of Microarray Data

In this example, the gene expression data were preprocessed by normalization, background correction, and batch effect correction before analysis of differential expression of genes and development of predictive models. Raw microarray data files were generated from all samples after they were ran on the whole genome DASL HT platform. Researchers used GenomeStudio to output a text sample probe file and control probe file with the following data: summarized expression level (AVG signal), standard error of the bead replicates (BEAD STDERR), average number of beads (Avg_NBEADS) and the detection p-value for a target gene being detected above background (Detection Pval). All subsequent analyses were performed using R and Bioconductor. Control probes and sample probes were used to pre-process (normalization and background correction) and to assess quality control using Bioconductor's lumi and limma packages. A specific pre-processing package (neqc) allowed for non-parametric background correction followed by quantile normalization using both control and sample probes. Researchers determined batch effects by chip array during the microarray processing using ComBat, an empirical Bayes method for removing batch effects. Expression levels were further adjusted for chip and shipment (each shipment consisted of several chip arrays).

Validation of Identified Genes in External Datasets

For validation of the identified genes, external datasets were used from 3 different studies that used whole-genome gene expression of PCa tumors. Genomic and clinical data for these studies were obtained from the Gene Expression Omnibus (GEO) (GSE46691, GSE21032, GSE41410). All three studies used the Affymetrix Human Exon 1.0 ST array to obtain gene expression data. PARTEK® (Copyright, Partek Inc. Copyright, Partek Inc. Partek and all other Partek Inc. product or service names are registered trademarks or trademarks of Partek Inc., St. Louis, Mo., USA.), was used to extract the raw data (Affymetrix CEL files) from GEO and was normalized through standard Robust Multi-array Average (RMA) method and background correction for Affymetrix arrays. The exon array has three types of annotations available, in decreasing order of reliability: core (using Refseq, full length mRNAs), extended (adding expressed sequence tags (ESTs), sytenic rat and mouse mRNAs), and full (adding ab-initio predictions). In order to ensure that all possible probes with good reliability were included in the validation, probes from the extended and full annotations were obtained for all genes in the selected models. Since literature on Affymetrix arrays shows that the probe intensity distributions among extended and full probes are almost indistinguishable, the probes from the full probeset annotation were used for validation purposes. Researchers identified all probes corresponding to each of the genes that corresponded to the probes included in researchers' final set of models and included those Affymetrix array probes in researchers' validation steps.

Using the corresponding expression data for the subset of probes identified for all genes included in researchers' identified models, and the patient population from each of the studies, repeated 5-fold cross-validation (CV) using elastic net ($\alpha$ set at=0.2, and no standardization of the probe variables) was performed for validation. To determine the best prediction of a parsimonious model, the $\lambda$ (LASSO penalty parameter) one standard error above the detected minimum $\lambda$ (with the lowest CV error) was used to obtain the average AUC across all CV runs. Genes for all possible predictive models (frequency threshold from stability selection 20%-80%) were assessed through cross validation using all data that was available for each dataset.

Results

Characteristics of Patients Included in the Discovery/Training Set

Gene expression profiles were generated for a total of 293 organ confined PCa patients who underwent radical prostatectomy at the University of Southern California. Of these patients 154 had no evidence of disease (NED) following surgery, indicating no recurrence of disease, 106 experienced biochemical recurrence (BCR) only and no further progression, and 33 patients experienced clinical recurrence of disease where local or distal metastasis was detected (CR) (Table 1).

TABLE 1

Characteristics of patients with gene expression profiles available

| | Controls | Recurrence cases | | p-value* | |
|---|---|---|---|---|---|
| | NED<br>n = 154 | BCR only<br>n = 106 | CR<br>n = 33 | NED vs.<br>CR | BCR vs.<br>CR |
| Age | | | | | |
| <60 | 54 (35) | 34 (32) | 4 (12) | 0.028 | 0.02 |
| 60-64 | 26 (25) | 26 (25) | 8 (24) | | |
| 65-69 | 39 (25) | 29 (27) | 8 (24) | | |
| 70+ | 35 (23) | 17 (16) | 13 (39) | | |
| PSA before surgery (ng/ml) | | | | | |
| ≤4 | 30 (19) | 5 (5) | 3 (9) | 0.215 | 0.571 |
| >4-10 | 84 (55) | 65 (61) | 18 (55) | | |
| >10-20 | 33 (21) | 28 (26) | 8 (24) | | |
| >20 | 7 (5) | 8 (8) | 4 (12) | | |
| Pathologic Gleason score | | | | | |
| ≤6 | 56 (36) | 37 (35) | 5 (15) | 0.01 | 0.012 |
| (3 + 4) or (2 + 5) | 60 (39) | 40 (38) | 11 (33) | | |
| (4 + 3) or (5 + 2) | 14 (9) | 16 (15) | 5 (15) | | |
| 8-10 | 24 (16) | 13 (12) | 12 (36) | | |
| Surgical margin status | | | | | |
| Negative | 119 (77) | 64 (60) | 24 (73) | 0.651 | 0.221 |
| Positive | 35 (23) | 42 (40) | 9 (27) | | |
| Race/ethnicity | | | | | |
| Non-Hispanic White | 137 (89) | 90 (85) | 29 (88) | 0.255 | 0.685 |
| Hispanic | 12 (8) | 7 (7) | 1 (3) | | |
| African-American | 4 (3) | 3 (3) | 2 (6) | | |
| Asian/PI | 1 (1) | 6 (6) | 1 (3) | | |
| Clinical stage | | | | | |
| cT1 | 105 (68) | 78 (74) | 17 (52) | 0.089 | 0.035 |
| cT2 | 48 (31) | 27 (25) | 15 (45) | | |
| cT3 | 1 (1) | 1 (1) | 1 (3) | | |
| Pathologic stage | | | | | |
| T2a | 10 (6) | 12 (11) | 3 (9) | 0.819 | 0.849 |
| T2b | 9 (6) | 8 (8) | 1 (3) | | |

TABLE 1-continued

Characteristics of patients with gene expression profiles available

| | Controls | Recurrence cases | | p-value* | |
| --- | --- | --- | --- | --- | --- |
| | NED<br>n = 154 | BCR only<br>n = 106 | CR<br>n = 33 | NED vs.<br>CR | BCR vs.<br>CR |
| T2c | 134 (87) | 86 (81) | 29 (88) | | |
| T2 with unknown laterality | 1 | 0 | 0 | | |
| Prostatectomy year | | | | | |
| July 1988-July 1994 | 56 (37) | 34 (32) | 18 (55) | 0.093 | 0.039 |
| July 1994-March 2005 | 90 (59) | 67 (63) | 13 (39) | | |
| March 2005-June 2008 | 6 (4) | 5 (5) | 2 (6) | | |
| D'Amico risk groups (those with available clinical data: Gleason, stage, PSA) | | | | | |
| Low | 50 (40) | 26 (30) | 2 (8) | <0.001 | 0.039 |
| Intermediate | 60 (48) | 45 (52) | 11 (42) | | |
| High | 15 (12) | 16 (18) | 13 (50) | | |
| Neoadjuvant hormonal therapy | | | | | |
| No | 148 (96) | 98 (92) | 25 (76) | 0.001 | 0.024 |
| Yes | 6 (4) | 8 (8) | 8 (24) | | |
| Radiation therapy | | | | | |
| No | 135 (88) | 91 (86) | 26 (79) | 0.177 | 0.412 |
| Yes | 19 (12) | 15 (14) | 7 (21) | | |
| Adjuvant hormone therapy | | | | | |
| No | 151 (98) | 105 (99) | 33 (100) | . | . |
| Yes | 3 (2) | 1 (1) | 0 (0) | | |
| Median follow-up time (IQR) | 9.55 (6.61-15.25) | 3.12 (1.78-5.79) | 5.83 (4.18-8.69) | | |

Abbreviations:
No evidence of disease (NED),
biochemical recurrence cases (BCR),
clinical metastatic recurrence (CR)
*Fisher's Exact p-value Comparing the characteristics between NED and CR patients, CR patients were older (age 70+, 39% CR versus 23% NEDs), had higher Gleason score (Gleason 8-10, 36% CR versus 16% NEDs, p=0.01), and more had neo-adjuvant hormonal therapy prior to surgery (24% CR versus 4% NEDs). CR patients were also more likely to be classified as high-risk according to the D'Amico risk classification using available diagnostic data prior to surgery (Table 1). When comparing BCR patients with CR patients, BCR only patients were younger (<60 years old, 32% BCR versus 12% CR), had lower pathologic Gleason scores (Gleason 6 or less, 35% NEDs versus 15% CR), were diagnosed with lower clinical stage (cT1, 74% BCR versus 52% CR), were more likely to be classified as low-risk according to the D'Amico risk classification (30% BCR versus 8% CR), and were less likely to receive neo-adjuvant hormonal therapy (8% BCR versus 24% CR). The median follow up time was 9.55 years for NEDs (controls), 3.12 years for BCR only patients, and 5.83 years for patients who experienced metastatic recurrence of disease.

Development of the Predictive Signature

After pre-processing of the gene expression data, a predictive signature of metastatic disease was developed using stability selection with elastic net regression. Only NED and CR patients were used to develop this predictive signature in order to find a genetic signature that could truly discriminate between indolent and aggressive disease. Elastic net regression was applied to each of 500 data sets obtained by subsampling the original data. After subsampling was completed, the probe sets obtained using stability frequency thresholds from 20% to 80% were determined and in turn evaluated using elastic net regression with repeated cross validation. A frequency threshold of 20% was the most liberal and included all genes that were seen among at least 20% of the subsample datasets, with a higher potential of including false positive markers, while a frequency threshold of 80% was the most stringent criteria picking genes that were seen among at least 80% of the subsample datasets. All stability selection runs force-included clinical variables (Gleason score, operation year, pre-operative PSA level, and age at surgery). The number of genes in the models therefore ranged from 163 (20% frequency threshold) to 3 genes (80% threshold).

Figure 2:
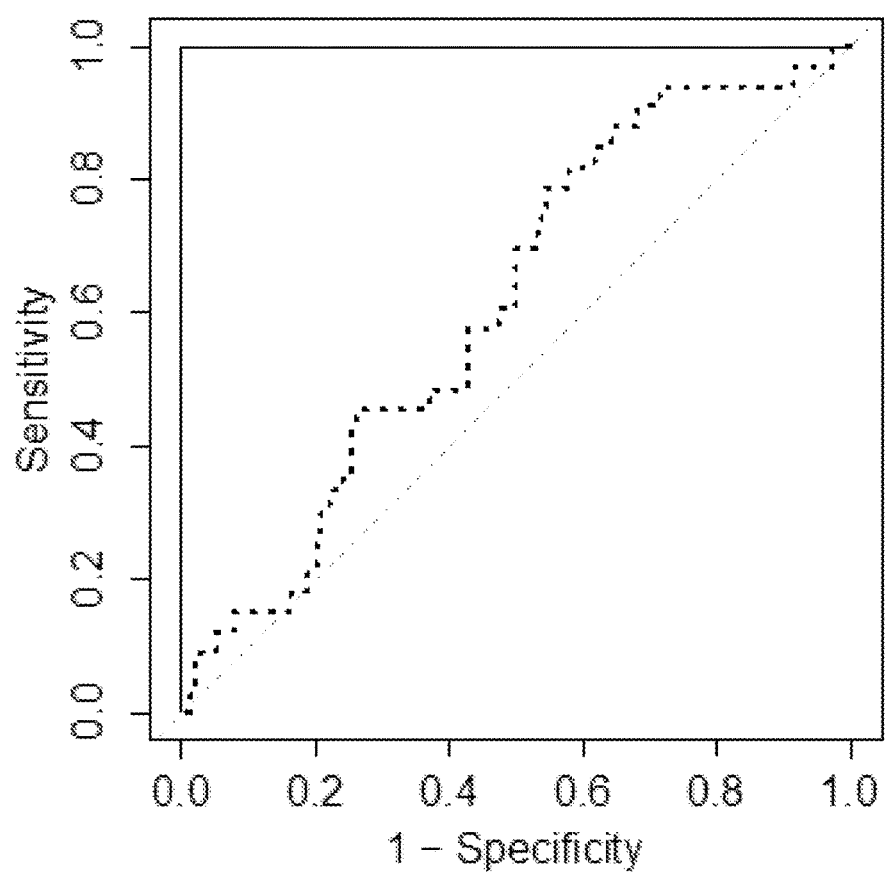
FIG. 2 shows ROC curves derived from repeated 5-fold cross-validation: 28 gene model versus clinical variables only model. The gene signature (solid line) has almost perfect predictive ability (AUC=0.99) and shows a major improvement over the model with just clinical variables. The ROC curve of the model with only clinical variables (Gleason score, pre-operative PSA level, and age) (dashed line) has an AUC=0.66.

The next step would be to apply the models to a test set in order to determine predictive ability based on AUC. However, since researchers' training set of 154 NED and 33 CR was not large enough to split into training and validation sets, researchers minimized the overoptimistic bias due to fitting and estimating the model AUC in the same data, by using elastic net with repeated 5-fold cross-validation on the entire training data. Each gene model at each threshold was evaluated to determine predictive ability by determining the average AUC across 10 cross-validations. The model at 50% frequency threshold with 28 genes including clinical variables (Gleason score, operation year, pre-operative PSA level, and age) showed the best prediction in the cross-validation. The ROC plot comparing the ROC curves of the 28-gene model and clinical variables (Gleason score, PSA level, age) alone show the improvement of prediction when using the genetic signature (FIG. 2). The list of signature genes (targets) included in this 28-gene model is included in Table 2. The same signature genes are presented in Table 3 sorted by the FDR-adjusted p-value comparing the NED patients and CR patients. In Table 3, genes that had been previously reported as associated with PCa progression and/or metastasis are marked by asterisks. The biological processes associated with each of the genes that correspond to these targets genes are listed in Table 4.

The model at 50% frequency threshold with 28 genes is obtained by fitting a logistic regression using stability selection with elastic net regression. The gene expression variables are regularized, and the clinical variables are forced without regularization. A preliminary set of regression coefficients for the model including the 28 genes and the clinical variables are shown in Table 5. The form of the logistic model reflects the model described above. One skilled in the art recognizes that the coefficients can be adjusted to improve the predictive power of the model, which can be achieved by more training and/or validating data. Improvement to the model may also be achieved by adjusting gene variable selection parameters discussed above.

TABLE 2

List of targets included in CR risk predictive model

| Rank in stability selection | Illumina Probe ID on WG-DASL HT platform | Gene symbol | Gene name | Entrez gene Cytogenetic band | Expression changes involved in the following cancers | Direction of expression (CR: NED) | Fold Change (CR: NED) |
|---|---|---|---|---|---|---|---|
| 1 | ILMN_2394841 | NKX2-1 (alias TTF-1) | NK2 homeobox 1 | 14q13 | Lung, thryoid, T-cell lymphoma | ↑ | 4.279 |
| 2 | ILMN_1655637 | UPK1A | uroplakin 1A | 19q13.3 | Bladder, esphagous, pancreas | ↑ | 2.580 |
| 3 | ILMN_1733963 | ADRA2C | Alpha-2-adrenergic receptor | 4p16.3 | Cervical, ovarian, melanoma, sarcoma, prostate, colorectal | ↓ | -2.503 |
| 4 | ILMN_2358714 | ABCC11 (alias MRP8) | ATP-binding cassette transporter, sub-family C, member 11 | 16q12.1 | Breast, colorectal, leukemia | ↑ | 2.387 |
| 5 | ILMN_1655915 | MMP11 | Matrix metalloproteinase-11 | 22q11.23 | Bladder, breast, colorectal, esophageal, gastric, kidney, lung, melanoma, ovarian | ↑ | 3.422 |
| 6 | ILMN_2400759 | CPVL | Carboxypeptidase, vitellogenic-like | 7p15.1 | Breast, leukemia, bladder, melanoma, sarcoma, lymphoma, brain and CNS | ↑ | 2.213 |
| 7 | ILMN_1723439 | ZYG11A | Zyg-11 family member A, cell cycle regulator | 1p32.3 | Lymphoma | ↑ | 4.314 |
| 8 | ILMN_1723115 | CLEC4F | C-type lectin domain family 4, member F | 2p13.3 | Liver, pancreas | ↑ | 2.962 |
| 9 | ILMN_1709333 | OAS2 | 2-5-oligoadenylate synthetase 2 | 12q24.2 | Breast, colorectal, kidney, leukemia, ovarian, sarcoma, lover, brain/CNS | ↓ | -2.369 |
| 10 | ILMN_1795484 | PGC | Progastricsin (pepsinogen C) | 6p21.1 | Gastric, colorectal, leukemia, lung, sarcoma | ↓ | -3.937 |
| 11 | ILMN_2264177 | UPK3B | Uroplakin 3B | 7q11.2 | Bladder, ovarian, pancreatic | ↑ | 2.245 |
| 12 | ILMN_1687216 | PCBP3 | Poly(rc) binding protein 3 | 21q22.3 | Bladder, lymphoma, ovarian, pancreatic | ↑ | 2.093 |
| 13 | ILMN_2396672 | ABLIM1 | Actin binding LIM protein 1 | 10q25 | Bladder, brain/CNS, breast, colorectal, esophageal, gastric, head/neck, kidney, leukemia, lung, lymphoma, melanoma, ovarian, prostate, sarcoma | ↓ | -2.576 |
| 14 | ILMN_1761820 | EDARADD | EDAR-associated death domain | 1q24.3 | Bladder, lung, ovarian | ↑ | 3.013 |
| 15 | ILMN_2161848 | GPR81 | G protein coupled receptor-81 | 12q24.31 | Breast, esophageal, gastric, kidney, lung, sarcoma | ↓ | -2.851 |
| 16 | ILMN_2330170 | MYBPC1 | Myosin binding protein C | 12q23.2 | Breast, esophageal, gastric, kidney, lung, sarcoma | ↓ | -2.754 |
| 17 | ILMN_1670708 | F10 | Coagulation factor X | 13q34 | Bladder, breast, lung, prostate, sarcoma, head and neck, cervical, colorectal | ↓ | -2.099 |
| 18 | ILMN_1702604 | KCNA3 | Potassium voltage-gated channel, shaker-related subfamily, member 3 | 1p13.3 | Kideny, leukeia, lymphoma, myeloma, sarcoma | ↑ | 2.375 |
| 19 | ILMN_1806754 | GLDC | Glycine dehydrogenase | 9p22 | Bladder, ovarian, kidney, breast, leukemia, cervical | ↑ | 3.147 |
| 20 | ILMN_1666776 | KCNQ2 | Potassium voltage-gated channel, KQT-like subfamily, member 2 | 20q13.3 | Brain/CNS, kidney, leukemia, melanoma, myeloma, sarcoma | ↓ | -2.481 |
| 21 | ILMN_1678799 | RAPGEF1 | Rap guanine nucleotide exchange factor (GEF) 1 | 9q34.3 | Kidney, melanoma, sarcoma, leukemia | ↑ | 2.249 |

TABLE 2-continued

List of targets included in CR risk predictive model

| Rank in stability selection | Illumina Probe ID on WG-DASL HT platform | Gene symbol | Gene name | Entrez gene Cytogenetic band | Expression changes involved in the following cancers | Direction of expression (CR: NED) | Fold Change (CR: NED) |
|---|---|---|---|---|---|---|---|
| 22 | ILMN_1680874 | TUBB2B | Tubulin, beta 2B class IIb | 6p25 | Bladder, brain/CNS, gastric, kidney, lung, lymphoma, melanoma, sarcoma | ↑ | 2.181 |
| 23 | ILMN_1766334 | MB | Myoglobin | 22q13.1 | Colorectal, head/neck, kidney, lung, lymphoma, melanoma | ↓ | −2.150 |
| 24 | ILMN_1710622 | DUOXA1 | Dual oxidase maturation factor 1 | 15q21.1 | Bladder, cervical, head/neck, lung | ↑ | 2.511 |
| 25 | ILMN_1660275 | C2orf43 | Chromosome 2 open reading frame 43 | 2p24.1 | Kidney, brain/CNS | ↓ | −2.623 |
| 26 | ILMN_1690289 | DUOX1 | Dual oxidase 1 | 15q15.3 | Bladder, cervical, esophageal, head/neck, kidney, lung, melanoma | ↑ | 3.143 |
| 27 | ILMN_3239648 | PCA3 | Prostate cacner antigen 3 (non-protein coding) | 9q21.2 | Prostate (overexpression) | ↓ | −2.019 |
| 28 | ILMN_1665033 | NPR3 | Natriuretic peptide receptor C/guanylate cyclase C | 5p14-p13 | Breast, colorectal, esophageal, head/neck, kidney, leukemia, lung, melanoma, sarcoma | ↓ | −2.533 |

*Data from Oncomine ™ and includes studies on cancers that had at least 2 fold change in the specific gene, in the top 10% of their differentially expressed gene lists, and in the same direction as found in our data.

TABLE 3

List of Signature Genes Sorted by p-value of Comparing NED and CR Groups

| Rank in Stability Selection | Gene symbol | Entrez gene Cytogenetic band | Fold Change (FC) (CR: NED) | FDR adjusted p-value |
|---|---|---|---|---|
| 7 | ZYG11A | 1p32.3 | 4.314 | 0.00018013 |
| 5 | MMP11 | 22q11.23 | 3.422 | 0.000556041 |
| 16 | MYBPC1 | 12q23.2 | -2.754 | 0.001967015 |
| 26 | DUOX1 | 15q15.3 | 3.143 | 0.008577907 |
| 14 | EDARADD | 1q24.3 | 3.013 | 0.013605825 |
| 10 | PGC | 6p21.1 | -3.937 | 0.018124745 |
| 15 | GPR81 | 12q24.31 | -2.851 | 0.019257234 |
| 1 | NKX2-1 | 14q13 | 4.279 | 0.024824283 |
| 13 | ABLIM1* | 10q25 | -2.576 | 0.024824283 |
| 4 | ABCC11 | 16q12.1 | 2.387 | 0.03107589 |
| 25 | C2orf43 | 2p24.1 | -2.623 | 0.033847114 |
| 24 | DUOXA1 | 15q21.1 | 2.511 | 0.042346696 |
| 19 | GLDC | 9p22 | 3.147 | 0.043043058 |
| 8 | CLEC4F | 2p13.3 | 2.962 | 0.044130058 |
| 18 | KCNA3 | 1p13.3 | 2.375 | 0.077361905 |
| 11 | UPK3B | 7q11.2 | 2.245 | 0.081098847 |
| 2 | UPK1A | 19q13.3 | 2.58 | 0.092767916 |
| 3 | ADRA2C* | 4p16.3 | -2.503 | 0.092767916 |
| 9 | OAS2 | 12q24.2 | -2.369 | 0.097135897 |
| 20 | KCNQ2 | 20q13.3 | -2.481 | 0.120182058 |
| 22 | TUBB2B | 6p25 | 2.181 | 0.135382441 |
| 28 | NPR3 | 5p14-p13 | -2.533 | 0.141039241 |
| 12 | PCBP3 | 21q22.3 | 2.093 | 0.143249926 |
| 21 | RAPGEF1 | 9q34.3 | 2.249 | 0.153617744 |
| 23 | MB | 22q13.1 | -2.15 | 0.182105622 |
| 27 | PCA3* | 9q21.2 | -2.019 | 0.202645242 |
| 6 | CPVL | 7p15.1 | 2.213 | 0.219670486 |
| 17 | F10* | 13q34 | -2.099 | 0.228298134 |

*Genes that have been reported to be associated with PCa progression and/or metastasis.

TABLE 4

Biological processes of the 28 genes in the USC predictive signature

| Biological Process (Gene Ontology Accession #) | # of genes involved | % of the 28 genes involved | Genes in the USC 28-gene model corresponding to their biological process |
|---|---|---|---|
| Metabolic process (GO: 0008152) | 13 | 52.00% | ADRA2C C2orf43 MYBPC1 OAS2 PCBP3 NKX2-1 GLDC PGC NPR3 F10 ABCC11 MMP11 CPVL |
| Cellular process (GO: 0009987) | 12 | 48.00% | ADRA2C KCNQ2 CLEC4F MYBPC1 TUBB2B PCBP3 ABLIM1 KCNA3 RAPGEF1 F10 UPK1A CPVL |
| Cell communication (GO: 0007154) | 9 | 36.00% | ADRA2C KCNQ2 CLEC4F MYBPC1 PCBP3 KCNA3 RAPGEF1 UPK1A CPVL |
| Transport (GO: 0006810) | 8 | 32.00% | ADRA2C KCNQ2 MB CLEC4F TUBB2B PCBP3 KCNA3 ABCC11 |
| System process (GO: 0003008) | 8 | 32.00% | ADRA2C KCNQ2 MB MYBPC1 PCBP3 KCNA3 UPK1A ABCC11 |
| Response to stimulus (GO: 0050896) | 7 | 28.00% | ADRA2C CLEC4F OAS2 PGC F10 UPK1A ABCC11 |
| Immune system process (GO: 0002376) | 7 | 28.00% | ADRA2C CLEC4F OAS2 F10 DUOX1 UPK1A ABCC11 |
| Developmental process (GO: 0032502) | 4 | 16.00% | MYBPC1 TUBB2B ABLIM1 NKX2-1 |
| Cell cycle (GO: 0007049) | 3 | 12.00% | TUBB2B PCBP3 RAPGEF1 |
| Cell adhesion (GO: 0007155) | 3 | 12.00% | CLEC4F MYBPC1 UPK1A |
| Cellular component organization (GO: 0016043) | 2 | 8.00% | TUBB2B ABLIM1 |
| Apoptosis (GO: 0006915) | 2 | 8.00% | ADRA2C PCBP3 |
| Reproduction (GO: 0000003) | 2 | 8.00% | F10 UPK1A |
| Regulation of biological process (GO: 0050789) | 1 | 4.00% | ADRA2C |
| Generation of precursor metabolites and energy (GO: 0006091) | 1 | 4.00% | DUOX1 |

TABLE 5

Preliminary Coefficients of Logistic Regression Model

| Variable | Model coefficient |
| --- | --- |
| ILMN_2358714 | 1.68498796 |
| ILMN_2396672 | −0.65616286 |
| ILMN_1733963 | −1.71491246 |
| ILMN_1660275 | −0.5363761 |
| ILMN_1723115 | 1.64143843 |
| ILMN_2400759 | 1.11362837 |
| ILMN_1690289 | 0.65429861 |
| ILMN_1710622 | 0.24135106 |
| ILMN_1761820 | 0.46879662 |
| ILMN_1670708 | −1.0486651 |
| ILMN_1806754 | 0.62010735 |
| ILMN_2161848 | −0.95741656 |
| ILMN_1702604 | 1.29156659 |
| ILMN_1666776 | −1.23284696 |
| ILMN_1766334 | −0.98892062 |
| ILMN_1655915 | 0.91947751 |
| ILMN_2330170 | −0.90696197 |
| ILMN_2394841 | 0.79762981 |
| ILMN_1665033 | −0.10751979 |
| ILMN_1709333 | −1.58161855 |
| ILMN_3239648 | 0.01388272 |
| ILMN_1687216 | 0.76483019 |
| ILMN_1795484 | −0.15331283 |
| ILMN_1678799 | 0.10999766 |
| ILMN_1680874 | 0.68754807 |
| ILMN_1655637 | 0.86842347 |
| ILMN_2264177 | 2.43075623 |
| ILMN_1723439 | 1.28768629 |
| age | 0.18092473 |
| PGleason8-10 | −2.2205802 |
| PGleason <=6 | −8.31732756 |
| PSA | −0.03006761 |
| opyr(1989, 1991] | −13.47932917 |
| opyr(1991, 1993] | −2.8971255 |
| opyr(1993, 1995] | −1.07617411 |
| opyr(1995, 1997] | −16.8713435 |
| opyr(1997, 1999] | −12.68168657 |
| opyr(1999, 2001] | −10.27860005 |
| opyr(2001, 2003] | −8.30730895 |
| opyr(2003, 2005] | −6.62023639 |
| opyr(2005, 2007] | −11.43552129 |

Pgleason = pathological Gleason score
opyr = operation year
age = age at diagnosis
PSA = pre-operative PSA level Validation of Predictive Model Using External Datasets Three independent datasets were used for validation of the gene signature predictive of recurrence: a dataset from the May Clinic (MC), from Memorial Sloan Kettering Cancer Center (MSKCC), and from Erasmus Medical center (EMC). In order to use these data to validate researchers' findings, all Affymetrix probes corresponding to each gene in researchers' predictive models were identified and included in models.

Since the Mayo Clinic dataset included a large number of patients with a similar study design as this example, it was used as the primary validation dataset to assess researchers' potential predictive models. A drawback of this dataset is the fact that the only clinical variable reported in the GEO database was Gleason score. Therefore, researchers were unable to validate the model with all the clinical variables included in the final predictive model. Models derived from stability selection were first validated using their entire dataset (n=545). Repeated 5-fold cross validation was performed on all 10 possible predictive models with different percent thresholds including Gleason score, and the AUCs were compared to the AUC of a model that included only Gleason score. The model with only Gleason score had an AUC=0.72. After all models were evaluated using repeated cross validation, the highest AUC obtained was 0.75. The 28-gene model at 50% frequency threshold in stability selection performed the best without including genes that did not add much more to the predictive ability of the model. The AUC stabilized at this model, since lowering the frequency threshold did not continue to improve predictive ability after this point. Therefore, researchers locked the model with the 28-gene signature.

Validation of the USC 28-gene model was done in 3 separate datasets. As seen in Table 6, when using the Mayo clinic dataset, the 28 gene model with Gleason score yielded an AUC=0.75, a 3% increase above AUC=0.72 in the model with only Gleason score. Using the MSKCC expression data, the 28-gene model with clinical variables obtained an AUC=0.90, a 4% improvement over clinical variables alone with AUC=0.86. With the EMC dataset, the 28-gene model+ clinical variables yielded an AUC=0.82, a 6% improvement over clinical variables only with an AUC=0.76.

TABLE 6

Validation of the 28-gene model using 3 independent datasets

|  | MC (Erho et al., 2013) | MSKCC (B. S. Taylor et al., 2010) | EMC (Boormans et al., 2013) |
| --- | --- | --- | --- |
| Tissue used for gene expression and clinical outcomes | 333 PM (NED + BCR) vs. 212 PM (CR) | 131 PM vs. 19 tissue from MET lessons | 39 PM (non-CR) vs. 9 PM (CR) |
| USC 28 gene model + clinical variables | 0.75 (0.72-0.77) | 0.90 (0.86-0.94) | 0.82 (0.74-0.91) |
| Clinical variables only* | 0.72 (0.70-0.74) | 0.86 (0.82-0.91) | 0.76 (0.67-0.85) |

Abbreviations:

Primary tumors (PM),

No evidence of disease (no recurrence patients) (NED), clinical recurrence (CR), metastasis tissue (MET);

Mayo Clinic (MC),

Memorial Sloan-Kettering Cancer Center (MSKCC),

Erasmus Medical Center (EMC).

*Clinical variables in model: MC - Gleason score only; MSKCC - age at diagnosis, race/ethnicity, neo-adjuvant treatment and adjuvant treatment for all patients (no missing data); EMC - pathologic stage and Gleason score (no missing data).

This example shows that a novel gene-expression based classifier, which is identified using agnostic approaches from whole genome expression profiles. The classifier can improve upon the accuracy of clinical indicators to identify early stage (T2) localized patients at risk of clinical recurrence after radical prostatectomy. Validation in existing external datasets showed promising improvements in prediction of clinical metastatic prostate cancer in comparison with clinical indicators only. Further validation in other datasets may improve the predictive ability of this 28-gene panel.

What is claimed is:

1. A method for treating a patient with prostate cancer, the method comprising:
obtaining a biological sample from the patient, wherein the biological sample comprises a prostate tissue sample,
detecting expression levels of a collection of genes from the biological sample, wherein detecting expression levels of the collection of genes comprises hybridizing probes specific for each of the genes to nucleic acid molecules derived from the biological sample, wherein the collection of genes comprises a collection of signature genes, and
wherein said collection of signature genes comprises NKX2-1 and ABCC11;
correlating expression levels of said collection of signature genes with prostate-cancer related mortality to identify whether the patient is at risk of prostate-cancer related mortality; and
treating a patient at risk of prostate-cancer related mortality with one or more of radical prostatectomy, brachytherapy of the prostate, radiotherapy of the prostate, neoadjuvant hormone therapy for treating prostate cancer, and adjuvant hormone therapy for treating prostate cancer.

2. The method of claim 1, wherein said collection of signature genes comprises at least one additional gene selected from the group consisting of: UPK1A, MMP11, CPVL, ZYG11A, CLEC4F, OAS2, PGC, UPK3B, PCBP3, EDARADD, GPR81, MYBPC1, KCNA3, GLDC, KCNQ2, RAPGEF1, TUBB2B, MB, DUOXA1, C2orf43, DUOX1, and NPR3.

3. The method of claim 1, wherein said collection of signature genes comprises at least one additional gene selected from the group consisting of: UPK1A, ADRA2C, MMP11, CPVL, ZYG11A, CLEC4F, OAS2, and PGC.

4. The method of claim 1, wherein said collection of signature genes comprises at least one additional gene selected from the group consisting of: ZYG11A, MMP11, MYBPC1, DUOX1, EDARADD, PGC, GPR81, and ABLIM1.

5. The method of claim 1, wherein the expression levels of a collection of signature genes comprise gene expression levels measured at multiple times.

6. The method of claim 1, wherein detecting the expression levels comprises:
obtaining expressed nucleic acids from the biological sample; and
determining amounts of the expressed nucleic acids for sequences of the signature genes.

7. The method of claim 6, wherein determining the amounts of the expressed nucleic acids comprises performing quantitative PCR on nucleic acids having sequences of the expressed nucleic acids from the biological sample.

8. The method of claim 6, wherein determining the amounts of the expressed nucleic acids comprises applying nucleic acids having sequences of the expressed nucleic acids from the biological sample to a nucleic acid array.

9. The method of claim 6, wherein determining the amounts of the expressed nucleic acids comprises sequencing nucleic acids using a next generation sequencing technique.

10. The method of claim 6, further comprising random priming of mRNA to produce cDNA.

11. The method of claim 10, further comprising further comprising hybridizing the produced cDNA to oligonucleotides corresponding to the signature genes.

12. The method of claim 11, further comprising extending the oligonucleotides.

13. The method of claim 12, further comprising ligating the oligonucleotides.

14. The method of claim 13, further comprising fluorescently labeling the oligonucleotides in qPCR and determining the expression levels of the signature genes based on fluorescence levels of the labeled oligonucleotides.

15. The method of claim 1, further comprising microdissecting the prostate tissue sample using a laser capture microdissection.

16. The method of claim 1, wherein said collection of signature genes comprises at least one additional gene selected from the group consisting of: UPK1A, ADRA2C, MMP11, CPVL, ZYG11A, CLEC4F, OAS2, PGC, UPK3B, PCBP3, ABLIM1, EDARADD, GPR81, MYBPC1, F10, KCNA3, GLDC, KCNQ2, RAPGEF1, TUBB2B, MB, DUOXA1, C2orf43, DUOX1, PCA3 and NPR3.

17. The method of claim 1, wherein said collection of signature genes comprises at least two additional genes selected from the group consisting of: ZYG11A, MMP11, MYBPC1, DUOX1, EDARADD, PGC, GPR81, and ABLIM1.

18. The method of claim 1, wherein said collection of signature genes comprises at least three additional genes selected from the group consisting of: UPK1A, ADRA2C, MMP11, CPVL, ZYG11A, CLEC4F, OAS2, PGC, UPK3B, PCBP3, ABLIM1, EDARADD, GPR81, MYBPC1, F10, KCNA3, GLDC, KCNQ2, RAPGEF1, TUBB2B, MB, DUOXA1, C2orf43, DUOX1, PCA3, and NPR3.

19. The method of claim 1, wherein said collection of signature genes comprises at least three additional genes selected from the group consisting of: UPK1A, MMP11, CPVL, ZYG11A, CLEC4F, OAS2, PGC, UPK3B, PCBP3, EDARADD, GPR81, MYBPC1, KCNA3, GLDC, KCNQ2, RAPGEF1, TUBB2B, MB, DUOXA1, C2orf43, DUOX1, and NPR3.

20. The method of claim 1, wherein said collection of signature genes comprises at least three additional genes selected from the group consisting of: UPK1A, ADRA2C, MMP11, CPVL, ZYG11A, CLEC4F, OAS2, and PGC.

21. The method of claim 1, wherein said collection of signature genes comprises at least three additional genes selected from the group consisting of: ZYG11A, MMP11, MYBPC1, DUOX1, EDARADD, PGC, GPR81, and ABLIM1.

22. The method of claim 1, wherein detecting expression levels of a collection of signature genes comprises contacting nucleic acid molecules derived from the biological sample with at least two probes, each configured to hybridize to a signature gene.

23. The method of claim 1, wherein identifying whether the patient is at risk of prostate cancer-related mortality comprises determining the patient's risk of clinical recurrence of prostate cancer or the patient's risk of biochemical recurrence of prostate cancer or both.

24. The method of claim 1, wherein the patient's clinical stage is T2.

25. A method for treating a patient with prostate cancer, wherein the patient has undergone a radical prostatectomy, the method comprising:
   obtaining a biological sample from the patient, wherein the biological sample comprises a prostate tissue sample;
   detecting expression levels of a collection of genes from the biological sample, wherein detecting expression levels of the genes comprises hybridizing probes specific for each of the genes to nucleic acid molecules derived from the biological sample, wherein the genes comprise a collection of signature genes, and
      wherein said collection of signature genes comprises NKX2-1 and ABCC11;
   correlating expression level of said collection of signature genes with clinical recurrence of prostate cancer after radical prostatectomy to identify whether the patient is at risk of clinical recurrence of prostate cancer after radical prostatectomy; and
   treating a patient at risk of clinical recurrence of prostate cancer after radical prostatectomy with at least one of brachytherapy of the prostate, radiotherapy of the prostate, neoadjuvant hormone therapy for treating prostate cancer, and adjuvant hormone therapy for treating prostate cancer.

26. The method of claim 25, wherein identifying whether the patient is at risk of clinical recurrence of prostate cancer comprises determining the patient's risk of biochemical recurrence of prostate cancer.

27. The method of claim 25, wherein the patient's clinical stage is T2.

28. The method of claim 25, wherein said collection of signature genes comprises at least one additional gene selected from the group consisting of: UPK1A, ADRA2C, MMP11, CPVL, ZYG11A, CLEC4F, OAS2, PGC, UPK3B, PCBP3, ABLIM1, EDARADD, GPR81, MYBPC1, F10, KCNA3, GLDC, KCNQ2, RAPGEF1, TUBB2B, MB, DUOXA1, C2orf43, DUOX1, PCA3 and NPR3.

29. The method of claim 25, wherein said collection of signature genes comprises at least one additional gene selected from the group consisting of: UPK1A, MMP11, CPVL, ZYG11A, CLEC4F, OAS2, PGC, UPK3B, PCBP3, EDARADD, GPR81, MYBPC1, KCNA3, GLDC, KCNQ2, RAPGEF1, TUBB2B, MB, DUOXA1, C2orf43, DUOX1, and NPR3.

30. The method of claim 25, wherein said collection of signature genes comprises at least one additional gene selected from the group consisting of: UPK1A, ADRA2C, MMP11, CPVL, ZYG11A, CLEC4F, OAS2, and PGC.

31. A method comprising detecting expression levels of genes from a biological sample taken from an individual, wherein the biological sample comprises a prostate tissue sample, wherein the genes consist of NKX2-1, UPK1A, ADRA2C, ABCC11, MMP11, CPVL, ZYG11A, CLEC4F, OAS2, PGC, UPK3B, PCBP3, ABLIM1, EDARADD, GPR81, MYBPC1, F10, KCNA3, GLDC, KCNQ2, RAPGEF1, TUBB2B, MB, DUOXA1, C2orf43, DUOX1, PCA3 and NPR3.

* * * * *

UNITED STATES PATENT AND TRADEMARK OFFICE
CERTIFICATE OF CORRECTION

PATENT NO. : 10,364,469 B2
APPLICATION NO. : 15/111946
DATED : July 30, 2019
INVENTOR(S) : Mariana Carla Stern, Jacek Pinski and Jain-Bing Fan It is certified that error appears in the above-identified patent and that said Letters Patent is hereby corrected as shown below:

In the Claims

Column 50, Lines 9-10, "The method of claim 10, further comprising further comprising hybridizing" should read --The method of claim 10, further comprising hybridizing--

Signed and Sealed this
Twelfth Day of November, 2019

Andrei Iancu
*Director of the United States Patent and Trademark Office*